US008828372B2

(12) United States Patent
Arnaud et al.

(10) Patent No.: US 8,828,372 B2
(45) Date of Patent: Sep. 9, 2014

(54) COSMETIC COMPOSITION COMPRISING AT LEAST ONE VINYL POLYMER AND AT LEAST ONE OLEFIN COPOLYMER

(75) Inventors: Pascal Arnaud, L'Hay les Roses (FR); Annick Collette, St Maur des Fosses (FR)

(73) Assignee: L'Oreal, Paris (FR)

( * ) Notice: Subject to any disclaimer, the term of this patent is extended or adjusted under 35 U.S.C. 154(b) by 670 days.

(21) Appl. No.: 11/806,297

(22) Filed: May 31, 2007

(65) Prior Publication Data

US 2008/0003195 A1    Jan. 3, 2008

(30) Foreign Application Priority Data

May 31, 2006  (FR) ..................................... 06 51988

(51) Int. Cl.
| | | |
|---|---|---|
| *A61Q 1/02* | (2006.01) | |
| *A61K 8/90* | (2006.01) | |
| *A61K 8/91* | (2006.01) | |
| *A61Q 1/12* | (2006.01) | |
| *A61Q 1/10* | (2006.01) | |

(52) U.S. Cl.
CPC ... *A61K 8/90* (2013.01); *A61K 8/91* (2013.01); *A61Q 1/12* (2013.01); *A61Q 1/10* (2013.01); *A61Q 1/02* (2013.01)
USPC .......................... 424/78.03; 424/63; 424/401

(58) Field of Classification Search
None
See application file for complete search history.

(56) References Cited

U.S. PATENT DOCUMENTS

| | | | | |
|---|---|---|---|---|
| 4,929,644 | A | * | 5/1990 | Guilbeaux ..................... 514/642 |
| 5,221,534 | A | | 6/1993 | DesLauriers et al. |
| 5,449,519 | A | * | 9/1995 | Wolf et al. ..................... 424/401 |
| 5,547,658 | A | * | 8/1996 | Hansenne et al. .............. 424/59 |
| 5,605,679 | A | * | 2/1997 | Hansenne et al. .............. 424/59 |
| 5,874,069 | A | | 2/1999 | Mendolia et al. |
| 5,919,441 | A | | 7/1999 | Mendolia et al. |
| 5,981,680 | A | | 11/1999 | Petroff et al. |
| 6,051,216 | A | | 4/2000 | Barr et al. |
| 6,083,516 | A | * | 7/2000 | Curtis et al. .................. 424/401 |
| 6,184,407 | B1 | * | 2/2001 | Yoshitake et al. ............ 556/434 |
| 6,420,504 | B1 | * | 7/2002 | Yoshitake et al. ............ 526/279 |
| 7,829,073 | B2 | * | 11/2010 | Martin et al. ............... 424/78.03 |
| 2004/0013624 | A1 | * | 1/2004 | Mateu et al. .................. 424/70.7 |
| 2005/0014674 | A1 | * | 1/2005 | Liechty et al. .................... 512/1 |
| 2005/0031560 | A9 | * | 2/2005 | Simonnet et al. ............... 424/63 |

FOREIGN PATENT DOCUMENTS

| | | |
|---|---|---|
| EP | 1 034 776 A1 | 9/2000 |
| EP | 1 055 674 A1 | 11/2000 |
| EP | 1 086 683 B1 | 3/2001 |
| EP | 0 963 751 B1 | 9/2004 |
| EP | 1481661 * | 12/2004 |
| FR | 2 840 204 A1 | 12/2003 |
| FR | 2868295 * | 10/2005 |
| JP | 2-171154 | 7/1990 |
| JP | 2000-63225 | 2/2000 |
| JP | 2000-290138 | 10/2000 |
| JP | 2001-518929 | 10/2001 |
| JP | 2005-298500 | 10/2005 |
| WO | WO 03/045337 A2 | 6/2003 |

OTHER PUBLICATIONS

Product information, personal care Dow Corning FA 4002-ID (Mar. 25, 2009).*
French Search Report for FR 0651988, dated Jan. 26, 2007.
English language abstract of EP 1 034 776 A1, Sep. 13, 2000.
English language abstract of FR 2 840 204 A1, Dec. 5, 2003.
English language abstract of JP 2-171154, Feb. 7, 1990.
Japanese Office Action issued Jul. 31, 2012, in Patent Application No. 2007-143871 (English-language translation only).
Office Action issued Aug. 27, 2013, in Japanese Patent Application No. 2007-143871 (English-language translation only).

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

Disclosed herein is a make-up and/or care composition for keratin materials comprising a liquid fatty phase comprising i) at least one vinyl polymer comprising at least one carbosiloxane dendrimer-derived unit, and ii) at least one olefin copolymer. Also disclosed herein is a method for making up keratin materials comprising applying a composition of the present disclosure to the keratin materials. Further disclosed herein is a method for producing a make-up having at least one of improved color fastness, improved matte staying power, and/or improved transfer resistance, the method comprising applying a composition of the present disclosure to the keratin materials.

17 Claims, No Drawings

COSMETIC COMPOSITION COMPRISING AT LEAST ONE VINYL POLYMER AND AT LEAST ONE OLEFIN COPOLYMER

This application claims benefit of priority under 35 U.S.C. §119 to French Patent Application No. FR 0651988, filed May 31, 2006, the contents of which are also incorporated herein by reference.

Disclosed herein is a make-up and/or care composition for keratin materials, such as the skin, comprising a liquid fatty phase and at least one vinyl polymer comprising at least one carbosiloxane dendrimer-derived unit and at least one olefin copolymer.

Make-up cosmetic compositions such as foundations, lipsticks, mascaras, make-up products for the body, concealers, eye shadows, and/or powders generally comprise fatty substances such as oils and/or waxes, and a particulate phase generally comprising fillers and/or pigments. These compositions may thus be provided in a form chosen from anhydrous gels, sticks or batons, and soft pastes. They may also be provided in the form of a powder which may be chosen, for example, from loose, compact, and pressed powders. Make-up compositions may also comprise water or a hydrophilic phase, and may be provided in this case in a form chosen from oil-in-water emulsions, water-in-oil emulsions, and multiple emulsions, such as in the case of foundations and/or tinted creams.

Care compositions may be chosen, for example, from anti-sun compositions and deodorants.

Foundation compositions are commonly used to provide aesthetic color to the skin, for example, the face. These make-up products generally comprise oils, pigments, and/or fillers and optionally additives such as cosmetic and/or dermatological active agents.

These compositions, when they are applied to the skin, may have the disadvantage of transferring, that is to say, of at least partially forming a deposit, leaving marks on certain supports with which they may come into contact, for instance, clothing and the skin. The result is generally a poor staying power of the film applied, requiring the application of the composition to be repeated regularly. Moreover, the appearance of these unacceptable marks on, for example, shirt collars, can put some users off from using this type of make-up.

Furthermore, the sebum secreted by the skin over time also can modify the properties of the make-up. In particular, sebum does not generally promote adhesion of the make-up to the skin and the transfer of the make-up may thus be even greater, causing a substantial loss of the make-up remaining on the skin.

It would therefore be desirable to provide make-up compositions for keratin materials, such as the skin, which have the advantage of forming a transfer-resistant deposit, or do not form a deposit, at least in part, on the supports with which they come into contact (e.g., clothing, fabric, etc.).

Disclosed herein, therefore, is a novel route for formulating a cosmetic product which may make it possible to obtain improved make-up staying power, for example, color fastness, matte staying power properties, and/or transfer-resistance properties.

The present inventors have found that by introducing into make-up and/or care cosmetic compositions for keratin materials, such as the skin, a vinyl polymer comprising at least one carbosiloxane dendrimer-derived unit and at least one olefin copolymer, it is possible to produce a make-up product having improved staying power.

Disclosed herein is a make-up and/or care composition for keratin materials, such as the skin, comprising a liquid fatty phase comprising:
- at least one vinyl polymer comprising at least one carbosiloxane dendrimer-derived unit, and
- at least one olefin copolymer.

The composition according to the present disclosure may be comfortable to wear, may not show tacky feel, and may spread easily.

Also disclosed herein is a non-therapeutic method for making-up and/or caring for keratin materials comprising applying a composition of the present disclosure to the keratin materials.

Further disclosed herein is the use of a composition as defined herein for producing a make-up effect on keratin materials, the make-up effect having at least one of improved color fastness, improved matte staying power, and/or improved transfer-resistance.

Vinyl Polymer Crafted with a Carbosiloxane Dendrimer

The vinyl polymer(s) present in the composition of the present disclosure comprises at least one carbosiloxane dendrimer-derived unit.

The vinyl polymer(s) may comprise, for example, a backbone and at least one side chain which comprises a carbosiloxane dendrimer structure. As used herein, the term "carbosiloxane dendrimer structure" means a molecular structure comprising branched groups having high molecular masses, the structure having a high regularity in the radial direction starting from the bonding to the backbone. Such carbosiloxane dendrimer structures are described in the form of a highly branched siloxane-silylalkylene copolymer, for example, in Japanese Laid-Open Patent Application No. Kokai 9-171 154.

The vinyl polymer comprises at least one carbosiloxane dendrimer-derived unit which may be chosen from those of the following formula:

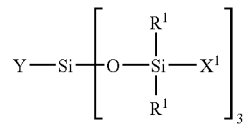

wherein:
R$^1$ is chosen from aryl groups and alkyl groups comprising from 1 to 10 carbon atoms,
X$^1$ is chosen from silylalkyl groups which, when i=1, are chosen from those of the following formula:

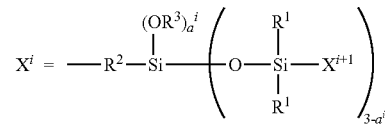

wherein
R$^1$ is defined above,
R$^2$ is chosen from alkylene groups comprising from 2 to 10 carbon atoms,
R$^3$ is chosen from alkyl groups comprising from 1 to 10 carbon atoms,
X$^{i+1}$ is chosen from hydrogen, alkyl groups comprising from 1 to 10 carbon atoms, aryl groups, and the silylalkyl groups defined above wherein i=i+1;

i is an integer ranging from 1 to 10 which represents the generation of the silylalkyl group, and $a^i$ is an integer ranging from 0 to 3; and Y is chosen from:

organic groups which can be polymerized with the aid of radicals chosen from organic groups comprising at least one group chosen from methacrylic and acrylic groups and which are chosen from compounds of the following formulas:

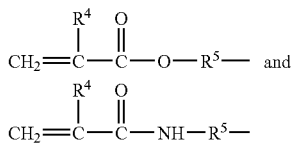

wherein:

$R^4$ is chosen from hydrogen and alkyl groups, and $R^5$ is chosen from alkylene groups comprising from 1 to 10 carbon atoms, such as methylene groups, ethylene groups, propylene groups, and butylene groups, and in at least one embodiment, methylene groups and propylene groups; and organic groups comprising a styryl group and which are chosen from compounds of the following formula:

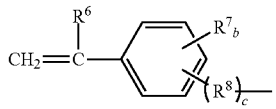

wherein:

$R^6$ is chosen from hydrogen and alkyl groups;

$R^7$ is chosen from alkyl groups comprising from 1 to 10 carbon atoms, such as methyl groups, ethyl groups, propyl groups, and butyl groups, and in at least one embodiment, methyl groups;

$R^8$ is chosen from alkylene groups comprising from 1 to 10 carbon atoms, such as methylene groups, ethylene groups, propylene groups, and butylene groups, and in at least one embodiment, ethylene groups;

b is an integer ranging from 0 to 4; and c is equal to 0 or 1, such that if c equals 0, $—(R^8)_c—$ represents a bond.

In at least one embodiment, $R^1$ is chosen from aryl groups and alkyl groups comprising from 1 to 10 carbon atoms, wherein the alkyl group is chosen, for example, from methyl groups, ethyl groups, propyl groups, butyl groups, pentyl groups, isopropyl groups, isobutyl groups, cyclopentyl groups, and cyclohexyl groups, and wherein the aryl group is chosen, for example, from phenyl groups and naphthyl groups. In another embodiment, $R^1$ may be chosen from methyl and phenyl groups, for example, methyl groups.

The vinyl polymer which comprises a carbosiloxane dendrimer structure may be the product of polymerization of:

(A) from 0 to 99.9 parts by weight of a vinyl-type monomer; and (B) from 100 to 0.1 parts by weight of a carbosiloxane dendrimer comprising an organic group which can be polymerized with the aid of radicals, and is chosen from compounds of formula:

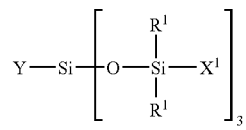

wherein

Y is an organic group which can be polymerized with the aid of radicals, $R^1$ is chosen from aryl groups and alkyl groups comprising from 1 to 10 carbon atoms, and $X^1$ is chosen from silylalkyl groups which, when i=1, are chosen from compounds of the following formula:

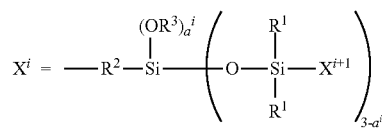

wherein $R^1$ is defined above, $R^2$ is chosen from alkylene groups comprising from 2 to 10 carbon atoms, $R^3$ is chosen from alkyl groups comprising from 1 to 10 carbon atoms, $X^{i+1}$ is chosen from hydrogen, alkyl groups comprising from 1 to 10 carbon atoms, aryl groups, and silylalkyl groups defined above wherein i=i+1;

i is an integer ranging from 1 to 10 which represents the generation of the silylalkyl group, and $a^i$ is an integer ranging from 0 to 3;

wherein the organic group which can be polymerized with the aid of radicals contained in the component (B) is chosen from:

organic groups comprising at least one group chosen from methacrylic groups and acrylic groups and which are chosen from compounds of the following formulas:

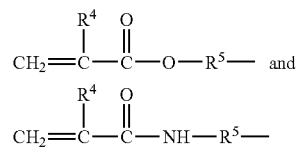

wherein $R^4$ is chosen from hydrogen and alkyl groups, and $R^5$ is chosen from alkylene groups comprising from 1 to 10 carbon atoms; and organic groups comprising a styryl group and which are chosen from compounds of the following formula:

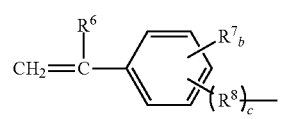

wherein $R^6$ is chosen from hydrogen and alkyl groups, $R^7$ is chosen from alkyl groups comprising from 1 to 10 carbon atoms, $R^8$ is chosen from alkylene groups comprising from 1 to 10 carbon atoms, b is an integer ranging from 0 to 4, and c equals 0 or 1, such that if c equals 0, $—(R^8)_c—$ represents a bond.

The vinyl-type monomer (A) in the vinyl polymer is a vinyl-type monomer comprising at least one vinyl group which can be polymerized with the aid of radicals. There is no particular limitation on what type of such monomers may be used. Non-limiting examples of suitable vinyl-type monomers include methyl methacrylate, ethyl methacrylate, n-propyl methacrylate, isopropyl methacrylate, and lower analogous alkyl methacrylates; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate, and higher analogous methacrylates; vinyl acetate, vinyl propionate, and lower analogous fatty acid vinyl esters; vinyl caproate, vinyl 2-ethylhexoate, vinyl laurate, vinyl stearate, and higher analogous fatty acid esters; styrene, vinyltoluene, benzyl methacrylate, phenoxyethyl methacrylate, vinylpyrrolidone, and analogous aromatic vinyl monomers; methacrylamide, N-methylolmethacrylamide, N-methoxymethylmethacrylamide, isobutoxymethoxymethacrylamide, N,N-dimethylmethacrylamide, and vinyl-type analogous monomers which comprise amide groups; hydroxyethyl methacrylate, hydroxypropyl alcohol methacrylate, and analogous vinyl-type monomers which comprise hydroxyl groups; acrylic acid, methacrylic acid, itaconic acid, crotonic acid, fumaric acid, maleic acid, and analogous vinyl-type monomers which comprise a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl and vinyl ether, cetyl and vinyl ether, 2-ethylhexyl and vinyl ether, and analogous vinyl-type monomers with ether bonds; methacryloxypropyltrimethoxysilane, polydimethylsiloxane having a methacrylic group at one of its molecular ends, polydimethylsiloxane having a styryl group at one of its molecular ends, and analogous silicone compounds comprising unsaturated groups; butadiene; vinyl chloride; vinylidene chloride; methacrylonitrile; dibutyl fumarate; anhydrous maleic acid; anhydrous succinic acid; methacryl and, glycidyl ether; organic salts of amines, ammonium salts, and alkali metal salts of methacrylic acid, itaconic acid, crotonic acid, maleic acid, and/or fumaric acid; unsaturated monomers which can be polymerized with the aid of radicals comprising a sulphonic acid group such as a styrenesulphonic acid group; quaternary ammonium salts derived from methacrylic acid such as 2-hydroxy-3-methacryloxypropyltrimethylammonium chloride; and methacrylic acid esters of alcohols comprising a tertiary amine group, such as esters of methacrylic acid and diethylamine.

Multifunctional vinyl-type monomers may also be used, for example, trimethylolpropane trimethacrylate, pentaerythritol trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropanetrioxyethyl methacrylate, tris-(2-hydroxyethyl)isocyanurate dimethacrylate, tris-(2-hydroxyethyl) isocyanurate trimethacrylate, polydimethylsiloxane capped with styryl groups possessing divinylbenzene groups at the two ends, and analogous silicone compounds comprising unsaturated groups.

The carbosiloxane dendrimer (B) is chosen from compounds of the following formula:

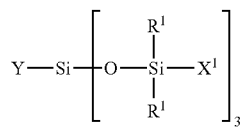

Examples of the organic group Y which can be polymerized with the aid of radicals include, but are not limited to, acryloxymethyl groups, 3-acryloxypropyl groups, methacryloxymethyl groups, 3-methacryloxypropyl groups, 4-vinylphenyl groups, 3-vinylphenyl groups, 4-(2-propenyl)phenyl groups, 3-(2-propenyl)phenyl groups, 2-(4-vinylphenyl) ethyl groups, 2-(3-vinylphenyl)ethyl groups, vinyl groups, allyl groups, methallyl groups, and 5-hexenyl groups.

According to one embodiment, $R^1$ is chosen from alkyl groups and aryl groups comprising from 1 to 10 carbon atoms, wherein the alkyl group may be chosen, for example, from methyl groups, ethyl groups, propyl groups, butyl groups, pentyl groups, isopropyl groups, isobutyl groups, cyclopentyl groups, and cyclohexyl groups; and the aryl group may be chosen, for instance, from phenyl groups and naphthyl groups. In at least one embodiment, $R^1$ may be chosen from methyl and phenyl groups, for example, methyl groups.

$X^1$ may be chosen from silylalkyl groups chosen from compounds of the following formula, when i is equal to 1:

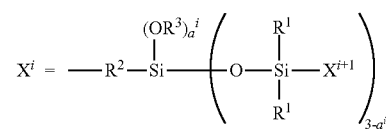

wherein $R^2$ is chosen from alkylene groups comprising from 2 to 10 carbon atoms, such as ethylene groups, propylene groups, butylene groups, hexylene groups, and analogous linear alkylene groups; methylmethylene groups, methylethylene groups, 1-methylpentylene groups, 1,4-dimethylbutylene groups, and analogous branched alkylene groups. According to one embodiment, $R^2$ may be chosen from ethylene, methylethylene, hexylene, 1-methylpentylene, and 1,4-dimethylbutylene groups. $R^3$ is chosen from alkyl groups comprising from 1 to 10 carbon atoms, such as methyl, ethyl, propyl, butyl, and isopropyl groups. $R^1$ is the same as defined above. $X^{i+1}$ is chosen from hydrogen, alkyl groups comprising from 1 to 10 carbon atoms, aryl groups, and silylalkyl groups wherein i=i+1. $a^i$ is an integer ranging from 0 to 3, and i is an integer ranging from 1 to 10 which indicates the number of generations which represents the number of repeats of the silylalkyl group.

For example, when the number of generations is equal to one, the carbosiloxane dendrimer may be represented by the first formula shown below, in which Y, $R^1$, $R^2$, and $R^3$ are defined above, $R^{12}$ is a hydrogen atom or is identical to $R^1$; and $a^1$ is identical to $a^i$. According to one embodiment, the mean total number of $OR^3$ groups in a molecule ranges from 0 to 7. When the number of generations is equal to 2, the carbosiloxane dendrimer may be represented by the second formula shown below, in which Y, $R^1$, $R^2$, $R^3$, and $R^{12}$ are defined above; and $a^1$ and $a^2$ represent the $a^i$ of the generation indicated. In another embodiment, the total mean number of $OR^3$ groups in a molecule ranges from 0 to 25. In the case where the number of generations is equal to 3, the carbosiloxane dendrimer is represented by the third formula shown below, wherein Y, $R^1$, $R^2$, $R^3$, and $R^{12}$ are defined above; and $a^1$, $a^2$ and $a^3$ represent the $a^i$ of the generation indicated. According to a further embodiment, the total mean number of $OR^3$ groups in a molecule ranges from 0 to 79.

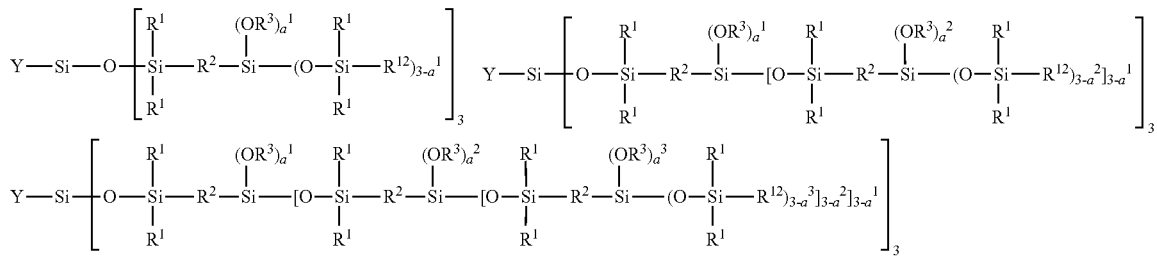
A carbosiloxane dendrimer comprising an organic group which can be polymerized with the aid of radicals may be chosen from compounds of the following structural formulas:
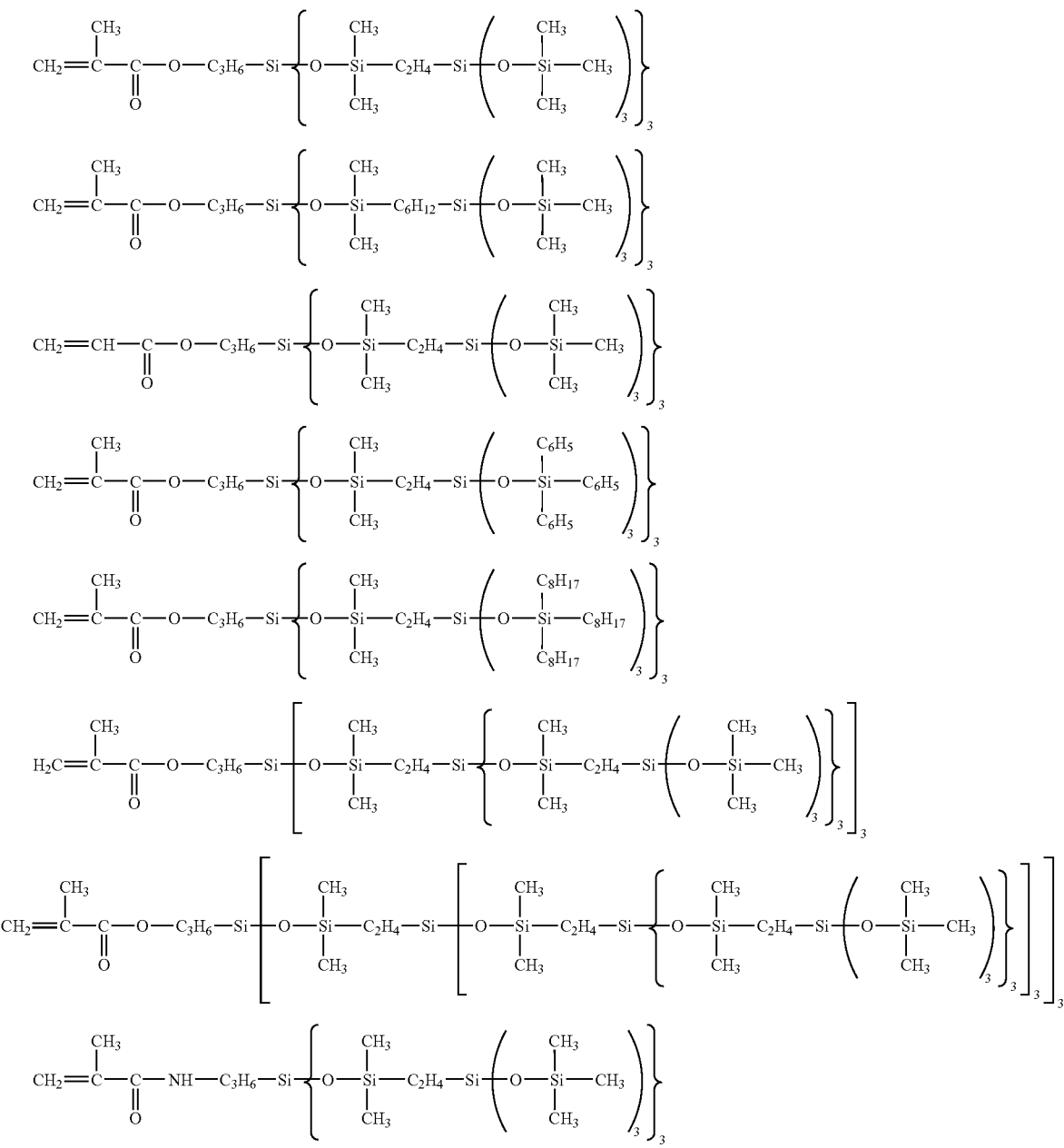

-continued

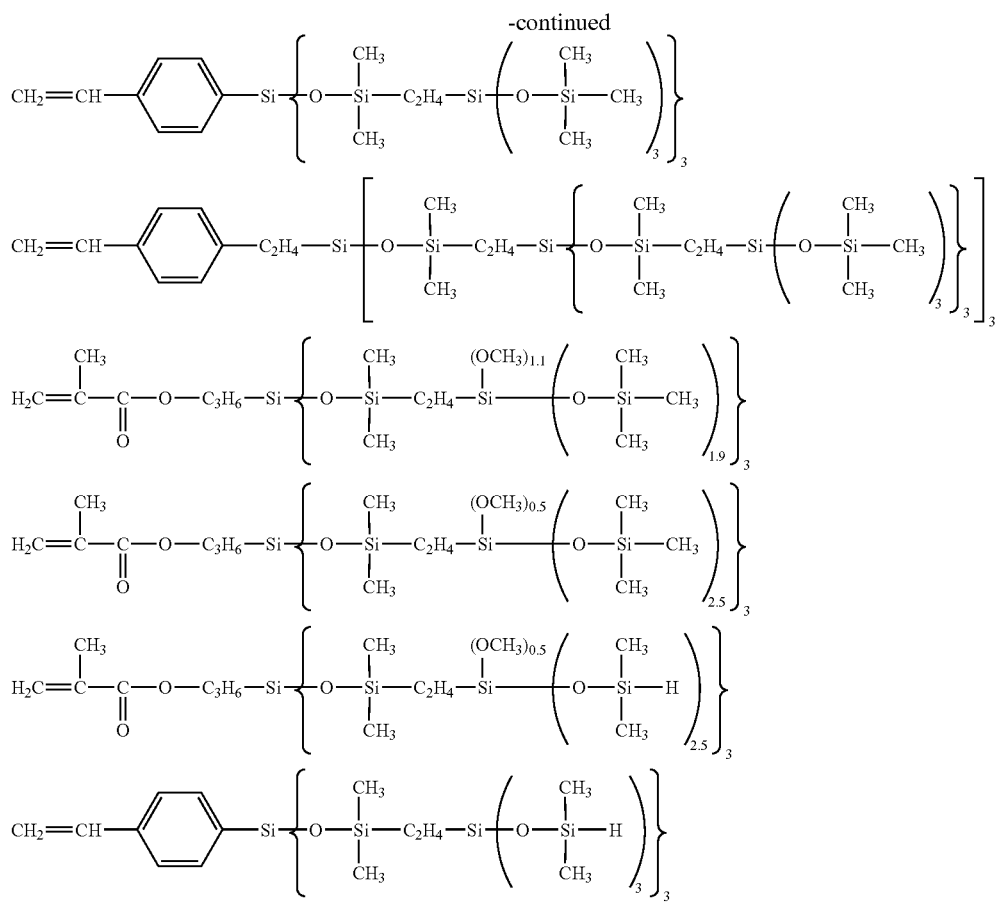

The carbosiloxane dendrimer may be manufactured according to the process for the manufacture of a branched silylalkylene siloxane described, for example, in Japanese Patent Application No. Hei 9-171 154. For example, it may be produced by subjecting to a hydrosilylation reaction an organosilicon compound which comprises a hydrogen atom linked to a silicon atom, represented by the following formula:

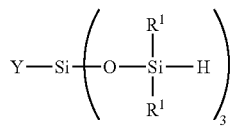

and an organosilicon compound which comprises an alkenyl group. In the above formula, the organosilicon compound may be chosen, for instance, from 3-methacryloxypropyltris-(dimethylsiloxy)silane, 3-acryloxypropyltris-(dimethylsiloxy)silane, and 4-vinylphenyltris-(dimethylsiloxy)silane. The organosilicon compound comprising an alkenyl group may be chosen, for example, from vinyltris-(trimethylsiloxy) silane, vinyltris-(dimethylphenylsiloxy)-silane, and 5-hexenyltris-(trimethylsiloxy)silane. The hydrosilylation reaction may be carried out in the presence of a chloroplatinic acid, a vinylsiloxane and platinum complex, and/or a catalyst analogous to a transition metal.

In the vinyl polymer which contains a dendrimer structure, the polymerization ratio between the components (A) and (B), in terms of ratio by weight between (A) and (B), may range, for example, from 0/100 to 99.9/0.1, such as from 1/99 to 99/1. A ratio between the components (A) and (B) of 0/100 means that the compound becomes a homopolymer of component (B).

The vinyl polymer contains a carbosiloxane dendrimer structure and may be obtained by copolymerization of the components (A) and (B), or by polymerization of component (B) alone. The polymerization may be chosen from free-radical polymerization and ionic polymerization. According to at least one embodiment, the polymerization is a free-radical polymerization. The polymerization may be carried out by causing a reaction between the components (A) and (B) in a solution for a period of time ranging from 3 to 20 hours in the presence of a radical initiator at a temperature ranging from 50° C. to 150° C.

Appropriate solvents for this purpose may be chosen, for instance, from hexane, octane, decane, cyclohexane, and analogous aliphatic hydrocarbons; benzene, toluene, xylene, and analogous aromatic hydrocarbons; diethyl ether, dibutyl ether, tetrahydrofuran, dioxane, and analogous ethers; acetone, methyl ethyl ketone, methyl isobutyl ketone, diisobutyl ketone, and analogous ketones; methyl acetate, ethyl acetate, butyl acetate, isobutyl acetate, and analogous esters; methanol, ethanol, isopropanol, butanol, and analogous alcohols; and octamethylcyclotetrasiloxane, decamethyl-cyclopentasiloxane, hexamethyidisiloxane, octamethyltrisiloxane, and analogous organosiloxane oligomers.

The radical initiator may be chosen from any compound known in the art for conventional free-radical polymerization reactions, such as 2,2'-azobis(isobutyronitrile), 2,2'-azobis(2-methylbutyronitrile), 2,2'-azobis(2,4-dimethylvaleronitrile), and analogous azobis-type compounds; benzoyl peroxide, lauroyl peroxide, tert-butyl peroxybenzoate, tert-butyl peroxy-2-ethylhexanoate, and analogous organic peroxides. These radical initiators may be used alone or in a combination of two or more. The radical initiators may be used in a quantity ranging from 0.1 to 5 parts by weight per 100 parts by weight of components (A) and (B).

A chain transfer agent may also be added. The chain transfer agent may be chosen, for example, from 2-mercaptoethanol, butylmercaptan, n-dodecylmercaptan, 3-mercaptopropyltrimethoxysilane, polydimethylsiloxanes comprising a mercaptopropyl group, and analogous mercapto-type compounds; methylene chloride, chloroform, carbon tetrachloride, butyl bromide, 3-chloropropyltrimethoxysilane, and analogous halogenated compounds.

In the manufacture of the vinyl-type polymer, after polymerization, the unreacted residual vinyl monomer may be removed under vacuum heating conditions.

To facilitate the preparation of a mixture of the raw material of cosmetic products, the number-average molecular mass of the vinyl polymer which comprises a carbosiloxane dendrimer may be chosen so as to range from 3000 to 2 000 000, for example, from 5000 to 800 000. It may be a liquid, a gum, a paste, a solid, a powder, or in any other form. In at least one embodiment, it is in the form of solutions prepared by dilution of a dispersion or of a powder in solvents.

The vinyl polymer may be a dispersion of a vinyl-type polymer having a carbosiloxane dendrimer structure in its molecular side chain, in a liquid, such as silicone oils, organic oils, alcohols, and water.

The vinyl polymer having a carbosiloxane dendrimer structure in its molecular side chain, in this embodiment, is the same as that described above. The liquid may be chosen from silicone oils, organic oils, alcohols, and water. The silicone oils may be chosen, for example, from dimethylpolysiloxanes having both molecular ends capped by trimethylsiloxy groups, methylphenylsiloxane and dimethylsiloxane copolymers having both molecular ends capped by trimethylsiloxy groups, methyl-3,3,3-trifluoropropylsiloxane and dimethylsiloxane copolymers having both molecular ends capped by trimethylsiloxy groups, and analogous non-reactive linear silicone oils; hexamethylcyclotrisiloxane, octamethylcyclotetrasiloxane, decamethylcyclopentasiloxane, dodecamethyl-cyclohexasiloxane; and analogous cyclic compounds. In addition to non-reactive silicone oils, modified polysiloxanes comprising functional groups such as silanol groups, amino groups, and polyether groups at the ends or inside molecular side chains may also be used.

The organic oils may be chosen, for instance, from paraffin oil, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, sweet almond oil, olive oil, cocoa butter, jojoba oil, gum oil, sunflower oil, soybean oil, camellia oil, squalane, castor oil, mink oil, cotton seed oil, coconut oil, egg yolk oil, beef tallow, lard, polypropylene glycol monooleate, neopentyl glycol 2-ethylhexanoate, or an analogous glycol ester oil; triglyceryl isostearate, triglyceride of a coconut oil fatty acid, and analogous polyhydric alcohol ester oils; polyoxyethylene and lauryl ether, polyoxypropylene and cetyl ether, and analogous polyoxyalkylene ethers.

The alcohol may be any alcohol appropriate for use together with a raw material for cosmetic products. For example, the alcohol may be chosen from methanol, ethanol, butanol, isopropanol, and analogous lower alcohols. A solution or a dispersion of alcohol may have a viscosity ranging from 10 to $10^9$ mPa at 25° C. To improve the properties of sensation during use in a cosmetic product, the viscosity may range from 100 to $5 \times 10^8$ mPa.s.

The solutions and dispersions may be easily prepared by mixing the vinyl polymer having a carbosiloxane dendrimer structure with at least one liquid chosen from silicone oils, organic oils, alcohols, and water. The liquids may be present in the step for polymerizing the vinyl-type polymer having a carbosiloxane dendrimer structure. In this case, the unreacted residual vinyl monomer may be completely removed by heat treatment of the solution or of the dispersion under atmospheric or reduced pressure. In the case of a dispersion, the dispersity of the vinyl-type polymer may be improved by adding at least one surfactant. The at least one surfactant may be chosen, for example, from hexylbenzenesulphonic acid, octylbenzenesulphonic acid, decylbenzenesulphonic acid, dodecylbenzenesulphonic acid, cetylbenzenesulphonic acid, myristylbenzenesulphonic acid, and anionic surfactants of the sodium salts of these acids; octyltrimethylammonium hydroxide, dodecyltrimethylammonium hydroxide, hexadecyltrimethylammonium hydroxide, octyidimethylbenzylammonium hydroxide, decyldimethylbenzylammonium hydroxide, dioctadecyldimethylammonium hydroxide, beef tallow-trimethylammonium hydroxide, coconut oil-trimethylammonium hydroxide, and analogous cationic surfactants; polyoxyalkylene alkyl ethers, polyoxyalkylenealkylphenols, polyoxyalkylene alkyl esters, polyoxyalkylene sorbitol esters, polyethylene glycol, polypropylene glycol, additives of diethylene glycol trimethylnonanol ethylene oxide, non-ionic surfactants of the polyester type, and mixtures thereof. In addition, the solvents and the dispersions may be combined with iron oxide and other analogous pigments appropriate for use with cosmetic products, as well as zinc oxide, titanium oxide, silicon oxide, mica, talc, and analogous inorganic oxides in powdered form. In the dispersion, the mean diameter of the vinyl-type polymer particles may range from 0.001 to 100 microns, for example, from 0.01 to 50 microns. In the case of particles having mean diameters above this range, the cosmetic product mixed with the emulsion may not have a sufficiently good sensation on the skin or to the touch, or adequate spreading properties or a pleasant sensation.

The vinyl polymer may be present in the dispersion or the solution in an amount ranging from 0.1 to 95% by weight, for instance, from 5 to 85% by weight. To facilitate the handling and the preparation of the mixture, the vinyl polymer may be present in the dispersion or solution in an amount ranging from 10 to 75% by weight.

The vinyl polymer may chosen, in at least one embodiment, from the polymers described in the examples of European Patent Application No. 0 963 751.

According to one embodiment, the vinyl polymer grafted with a carbosiloxane dendrimer may be the product of polymerization of:

(A) from 0.1 to 99 parts by weight of at least one monomer chosen from acrylate and methacrylate monomers; and
(B) from 100 to 0.1 parts by weight of at least one monomer chosen from acrylate and methacrylate monomers of a carbosiloxane dendrimer tri[tri(trimethylsiloxy)silylethyl dimethylsiloxy]silylpropyl.

The carbosiloxane dendrimer tri[tri(trimethylsiloxy)silylethyl dimethylsiloxy]silylpropyl is chosen from compounds of the following formulas:

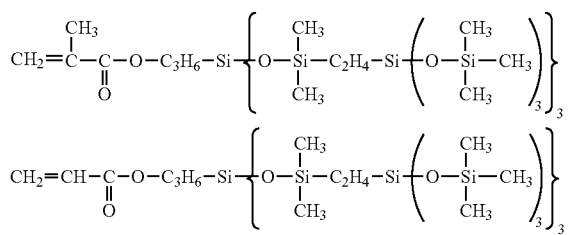

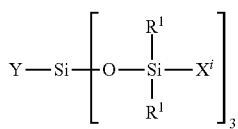

According to one embodiment, the vinyl polymer grafted with a carbosiloxane dendrimer may comprise at least one butyl acrylate monomer.

According to another embodiment, the vinyl polymer may additionally comprise at least one fluorinated organic group.

In at least one embodiment, the vinyl polymer may have a structure in which the polymerized vinylic units constitute the backbone and carbosiloxane dendritic structures as well as fluorinated organic groups are attached to side chains.

The fluorinated organic groups may be obtained by replacing with fluorine atoms all or part of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups, and of other alkyl groups comprising from 1 to 20 carbon atoms, as well as alkyloxyalkylene groups comprising from 6 to 22 carbon atoms.

The groups represented by the formula: $-(CH_2)_x-(CF_2)_y-R^{13}$ are non-limiting examples of fluoroalkyl groups obtained by replacing hydrogen atoms of alkyl groups with fluorine atoms. In the formula, the subscript "x" is an integer ranging from 0 to 3 and "y" is an integer ranging from 1 to 20. $R^{13}$ is chosen from atoms and groups chosen from hydrogen, fluorine, $-(CH(CF_3)_2-$, and $CF(CF_3)_2$. Such alkyl groups substituted with fluorine are exemplified, for instance, by linear or branched polyfluoroalkyl and perfluoroalkyl groups chosen from compounds of the following formulas:
$-CF_3$, $-C_2F_5$, $-nC_3F_7$, $-CF(CF_3)_2$, $-nC_4F_9$, $CF_2CF(CF_3)_2$, $-nC_5F_{11}$, $-nC_6F_{13}$, $-nC_8F_{17}$, $-CH_2CF_3$, $-(CH(CF_3)_2-$, $CH_2CH(CF_3)_2-CH_2(CF_2)_2F$, $-CH_2(CF_2)_3F$, $-CH_2(CF_2)_4F$, $-CH_2(CF_2)_6F$, $-CH_2(CF_2)_8F$, $-CH_2CH_2CF_3$, $-CH_2CH_2(CF_2)_2F$, $-CH_2CH_2(CF_2)_3F$, $-CH_2CH_2(CF_2)_4F$, $-CH_2CH_2(CF_2)_6F$, $-CH_2CH_2(CF_2)_8F$, $-CH_2CH_2(CF_2)_{10}F$, $-CH_2CH_2(CF_2)_{12}F$, $-CH_2CH_2(CF_2)_{14}F$, $-CH_2CH_2(CF_2)_{16}F$, $-CH_2CH_2CH_2CF_3$, $-CH_2CH_2CH_2(CF_2)_2F$, $-CH_2CH_2CH_2(CF_2)_2H$, $-CH_2(CF_2)_4H$, and $-CH_2CH_2(CF_2)_3H$.

The groups represented by the formula: $-CH_2CH_2-(CF_2)_m-CFR^{14}-[OCF_2CF(CF_3)]_n-OC_3F_7$ are non-limiting examples of fluoroalkyloxyfluoroalkylene groups obtained by replacing hydrogen atoms of the alkoxyalkylene groups with fluorine atoms. In the formula, the subscript "m" is equal to 0 or 1, "n" is an integer ranging from 0 to 5, and $R^{14}$ is chosen from fluorine and $CF_3$. Such fluoroalkyloxyfluoroalkylene groups are exemplified, for instance, by the perfluoroalkyloxyfluoroalkylene groups of the following formulas.
$-CH_2CH_2CF(CF_3)-[OCF_2CF(CF_3)]_n-OC_3F_7$ and
$-CH_2CH_2CF_2CF_2-[OCF_2CF(CF_3)]_n-OC_3F_7$.

The number-average molecular weight of the vinyl polymer used in the present invention may range, for example, from 3000 to 2 000 000, such as from 5000 to 800 000.

In at least one embodiment, this type of fluorinated vinyl polymer may be obtained by combining:
   at least one vinyl monomer (B) which does not have a fluorinated organic group in the molecule
   at least one vinyl monomer containing fluorinated organic groups in the molecule (A), and
   at least one carbosiloxane dendrimer (C) containing organic groups which can be polymerized by the free radical route, represented by the following formula (III):

$$Y-Si\left[-O-\underset{\underset{R^1}{|}}{\overset{\overset{R^1}{|}}{Si}}-X^i\right]_3$$

in which Y is an organic group which can be polymerized by the free radical route and $R^1$ and $X^i$ are defined above; and subjecting them to copolymerization.

The vinyl monomers (A) containing fluorinated organic groups in the molecule may be chosen, in at least one embodiment, from monomers of formula: $-(CH_2)=CR^{15}COOR^f$. In the formula, $R^{15}$ is chosen from hydrogen and methyl groups, $R^f$ is a fluorinated organic group, for example, the fluoroalkyl and fluoroalkyloxyfluoroalkylene groups described above. Non-limiting examples include compounds of the following formulas, wherein "z" is an integer ranging from 1 to 4. $CH_2=CCH_3COO-CF_3$. $CH_2=CCH_3COO-C_2F_5$. $CH_2=CCH_3COO-nC_3F_7$. $CH_2=CCH_3COO-CF(CF_3)_2$. $CH_2=CCH_3COO-nC_4F_9$. $CH_2=CCH_3COO-CF_2CF(CF_3)_2$. $CH_2=CCH_3COO-nC_5F_{11}$. $CH_2=CCH_3COO-nC_6F_{13}$. $CH_2=CCH_3COO-nC_8F_{17}$. $CH_2=CCH_3COO-CH_2CF_3$. $CH_2=CCH_3COO-CH(CF_3)_2$. $CH_2=CCH_3COO-CH_2CH(CF_3)_2$. $CH_2=CCH_3COO-CH_2(CF_2)_2F$. $CH_2=CCH_3COO-CH_2(CF_2)_3F$. $CH_2=CCH_3COO-CH_2(CF_2)_4F$. $CH_2=CCH_3COO-CH_2(CF_2)_6F$. $CH_2=CCH_3COO-CH_2(CF_2)_8F$. $CH_2=CCH_3COO-CH_2CH_2CF_3$. $CH_2=CCH_3COO-CH_2CH_2(CF_2)_2F$. $CH_2=CCH_3COO-CH_2CH_2(CF_2)_3F$. $CH_2=CCH_3COO-CH_2CH_2(CF_2)_4F$. $CH_2=CCH_3COO-CH_2CH_2(CF_2)_6F$. $CH_2=CCH_3COO-CH_2CH_2(CF_2)_8F$. $CH_2=CCH_3COO-CH_2CH_2(CF_2)_{10}F$. $CH_2=CCH_3COO-CH_2CH_2(CF_2)_{12}F$. $CH_2=CCH_3COO-CH_2CH_2(CF_2)_{14}F$. $CH_2=CCH_3COO-CH_2CH_2(CF_2)_{16}F$. $CH_2=CCH_3COO-CH_2CH_2CH_2CF_3$. $CH_2=CCH_3COO-CH_2CH_2CH_2(CF_2)_2F$. $CH_2=CCH_3COO-CH_2(CF_2)_2H$. $CH_2=CCH_3COO-CH_2(CF_2)_4H$. $CH_2=CCH_3COO-CH_2CH_2(CF_2)_3H$. $CH_2=CCH_3COO-CH_2CH_2CF(CF_3)-[OCF_2CF(CF_3)]_z-OC_3F_7$. $CH_2=CCH_3COO-CH_2CH_2CF_2CF_2-[OCF_2CF(CF_3)]_z-OC_3F_7$. $CH_2=CHCOO-CF_3$. $CH_2=CHCOO-C_2F_5$. $CH_2=CHCOO-nC_3F_7$. $CH_2=CHCOO-CF(CF_3)_2$. $CH_2=CHCOO-nC_4F_9$. $CH_2=CHCOO-CF_2CF(CF_3)_2$. $CH_2=CHCOO-nC_5F_{11}$. $CH_2=CHCOO-nC_6F_{13}$. $CH_2=CHCOO-nC_8F_{17}$. $CH_2=CHCOO-CH_2CF_3$. $CH_2=CHCOO-CH(CF_3)_2$. $CH_2=CHCOO-CH_2CH(CF_3)_2$. $CH_2=CHCOO-CH_2(CF_2)_2F$. $CH_2=CHCOO-CH_2(CF_2)_3F$. $CH_2=CHCOO-CH_2(CF_2)_4F$. $CH_2=CHCOO-CH_2(CF_2)_6F$. $CH_2=CHCOO-CH_2(CF_2)_8F$. $CH_2=CHCOO-CH_2CH_2CF_3$. $CH_2=CHCOO-CH_2CH_2(CF_2)_2F$. $CH_2=CHCOO-CH_2CH_2(CF_2)_3F$. $CH_2=CHCOO-CH_2CH_2(CF_2)_4F$. $CH_2=CHCOO-CH_2CH_2(CF_2)_6F$. $CH_2=CHCOO-CH_2CH_2(CF_2)_8F$. $CH_2=CHCOO-CH_2CH_2(CF_2)_{10}F$. $CH_2=CHCOO-CH_2CH_2(CF_2)_{12}F$. $CH_2=CHCOO-CH_2CH_2(CF_2)_{14}F$. $CH_2=CHCOO-CH_2CH_2(CF_2)_{16}F$. $CH_2=CHCOO-CH_2CH_2CH_2CF_3$. $CH_2=CHCOO-CH_2CH_2CH_2(CF_2)_2F$. $CH_2=CHCOO-CH_2CH_2(CF_2)_2H$. $CH_2=CHCOO-CH_2(CF_2)_4H$. $CH_2=CHCOO-CH_2CH_2(CF_2)_3H$. $CH_2=CHCOO-CH_2CH_2CF(CF_3)-[OCF_2CF(CF_3)]_z-OC_3F_7$. $CH_2=CHCOO-CH_2CH_2CF_2CF_2-[OCF_2CF(CF_3)]_z-OC_3F_7$.

According to one embodiment, the vinyl polymers may be chosen from: $CH_2=CHCOO-CH_2CH_2(CF_2)_6F$. $CH_2=CHCOO-CH_2CH_2(CF_2)_8F$. $CH_2=CCH_3COO-CH_2CH_2(CF_2)_6F$. $CH_2=CCH_3COO-CH_2CH_2(CF_2)_8F$. $CH_2=CHCOO-CH_2CF_3$. $CH_2=CCH_3COO-CH_2CF_3$ In another embodiment, the vinyl polymers may be chosen from: $CH_2=CHCOO-CH_2CF_3$, $CH_2=CCH_3COO-CH_2CF_3$.

The vinyl monomers (B) which do not contain fluorinated organic groups in the molecule may be any monomers having vinyl groups which can be polymerized by the free radical route, for example, methyl acrylate, methyl methacrylate, ethyl acrylate, ethyl methacrylate, n-propyl acrylate, n-propyl methacrylate, isopropyl acrylate, isopropyl methacrylate, and other lower alkyl acrylates and methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate, and other higher acrylates and methacrylates; vinyl acetate, vinyl propionate, and other lower fatty acid vinyl esters; vinyl butyrate, vinyl caproate, vinyl 2-ethylhexanoate, vinyl laurate, vinyl stearate, and other higher fatty acid esters; styrene, vinyltoluene, benzyl acrylate, benzyl methacrylate, phenoxyethyl acrylate, phenoxyethyl methacrylate, vinylpyrrolidone, and other aromatic vinyl monomers; dimethylaminoethyl acrylate, dimethylaminoethyl methacrylate, diethylaminoethyl acrylate, diethylaminoethyl methacrylate, and other amino-containing vinyl monomers, acrylamide, methacrylamide, N-methylolacrylamide, N-methylolmethacrylamide, N-methoxymethylacrylamide, N-methoxymethylmethacrylamide, isobutoxymethoxyacrylamide, isobutoxymethoxymethacrylamide, N,N-dimethylacrylamide, N,N-dimethylmethacrylamide, and other amide-containing vinyl monomers; hydroxyethyl acrylate, hydroxyethyl methacrylate, acrylic acid hydroxypropyl alcohol, methacrylic acid hydroxypropyl alcohol, and other hydroxy-containing vinyl monomers; acrylic acid, methacrylic acid, itaconic acid, crotonic acid, fumaric acid, maleic acid, and other carboxylic-containing vinyl monomers; tetrahydrofurfuryl acrylate, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether, and other vinyl monomers containing ether bonds; acryloxypropyltrimethoxysilane, methacryloxypropyltrimethoxysilane, polydimethylsiloxanes containing acryl or methacryl groups at one of the ends, polydimethylsiloxanes containing alkenylaryl groups at one of the ends and other silicone compounds containing unsaturated groups; butadiene; vinyl chloride; vinylidene chloride, acrylonitrile, methacrylonitrile; dibutyl fumarate; maleic anhydride; dodecylsuccinic anhydride; acryl glycidyl ether, methacryl glycidyl ether, 3,4-epoxycyclohexylmethyl acrylate, 3,4-epoxycyclohexylmethyl methacrylate, alkali metal salts, ammonium salts and the organic amine salts of acrylic acid, methacrylic acid, itaconic acid, crotonic acid, fumaric acid, maleic acid, and other unsaturated carboxylic acids which can be polymerized by the free radical route, unsaturated monomers which can be polymerized by the free radical route containing sulphonic acid groups such as styrenesulphonic acid and their alkali metal salts, their ammonium salts, and their organic, amine salts; quaternary ammonium salts derived from acrylic acid or methacrylic acid such as 2-hydroxy-3-methacryloxypropyltrimethylammonium chloride, and methacrylic acid esters of an alcohol containing a tertiary amine such as methacrylic acid diethylamine ester and their quaternary ammonium salts.

In another embodiment, the vinyl monomers (B) may be chosen from polyfunctional vinyl monomers, for example, trimethylolpropane triacrylate, trimethylolpropane trimethacrylate, pentaerythritol triacrylate, pentaerythritol trimethacrylate, ethylene glycol diacrylate, ethylene glycol dimethacrylate, tetraethylene glycol diacrylate, tetraethylene glycol dimethacrylate, polyethyleneglycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentylglycol diacrylate, neopentylglycol dimethacrylate, trimethylolpropanetrioxyethyl acrylate, trimethylolpropanetrioxyethyl methacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane in which the two ends of the molecular chain are blocked by alkenylaryl groups, and other silicone compounds containing unsaturated groups.

According to one embodiment, the ratio by weight in which the component (A) and the component (B) are copolymerized may range from 0.1:99.9 to 100:0, for example, from 1:99 to 100:0.

The carbosiloxane dendrimer (C) is represented by the formula (III) indicated above. In formula (III), Y is an organic group which can be polymerized by the radical route, whose type is not subject to any special limitations as long as it is an organic group which is capable of being subjected to a free radical addition reaction. Non-limiting examples of such groups include acryl- and methacryl-containing organic groups, alkenylaryl-containing organic groups, and alkenyl groups comprising from 2 to 10 carbon atoms of the following formulas:

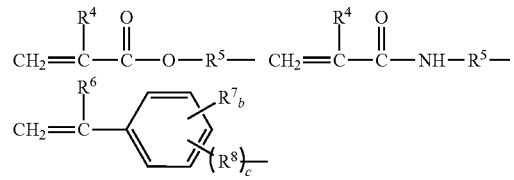

In the formulas above, $R^4$ and $R^6$, which may be identical or different, are chosen from hydrogen and methyl groups, $R^5$ and $R^8$, which may be identical or different, are chosen from alkylene groups comprising from 1 to 10 carbon atoms, and $R^7$ is chosen from alkyl groups comprising from 1 to 10 carbon atoms. The subscript "b" is an integer ranging from 0 to 4, and "c" is equal to 0 or 1. Examples of such organic groups which can be polymerized by the free radical route include, but are not limited to, acryloxymethyl, 3-acryloxypropyl, methacryloxymethyl, 3-methacryloxypropyl, 4-vinylphenyl, 3-vinylphenyl, 4-(2-propenyl)phenyl, 3-(2-propenyl)phenyl, 2-(4-vinylphenyl)ethyl, 2-(3-vinylphenyl)enyl, vinyl, allyl, methallyl, and 5-hexenyl.

The superscript "i" in the formulas above is an integer ranging from 1 to 10 and represents the number of generations of the silylalkyl group, i.e., the number of times that the silylalkyl group is repeated. Thus, the carboxyloxane dendrimer of this component with a number of generations of 1 is represented by the following formula:

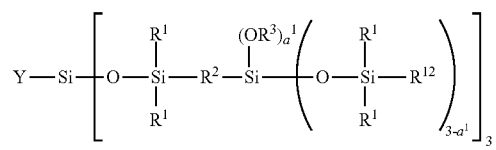

wherein Y, $R^1$, $R^2$, and $R^3$ are defined above and $R^{12}$ is a hydrogen atom or the same as $R^1$ described above. The subscript "$a^1$" is an integer ranging from 0 to 3, the mean total of "$a^1$" per molecule ranging from 0 to 7. The carbosiloxane dendrimers of this component with a number of generations of 2 are represented by the following formula:

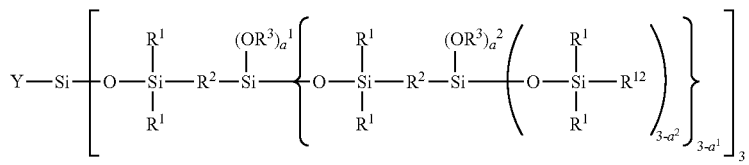

wherein Y, $R^1$, $R^2$, $R^3$, and $R^{12}$ are defined above and the subscripts "$a^1$" and "$a^2$" are integers ranging from 0 to 3, the mean total of "$a^1$" and of "$a^2$" per molecule ranging from 0 to 25).

The carbosiloxane dendrimers of this component with a number of generations of 3 are represented by the following formula:

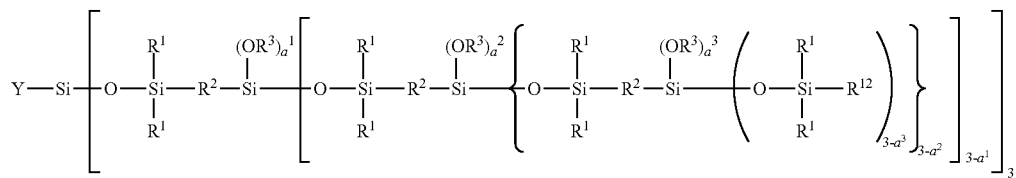

wherein Y, $R^1$, $R^2$, $R^3$, and $R^{12}$ are defined above and the subscripts "$a^1$", "$a^2$", and "$a^3$" are integers ranging from 0 to 3, the mean total of "$a^1$", "$a^2$", and "$a^3$" per molecule ranging 0 to 79).

According to at least one embodiment, the component (C) may be chosen from carbosiloxane dendrimers of the following formulas:

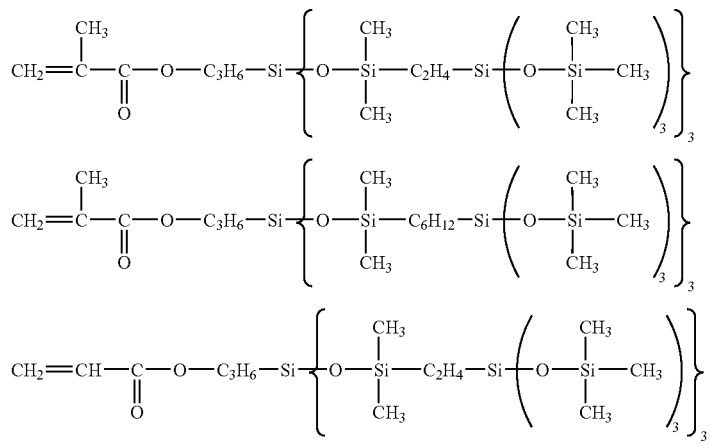

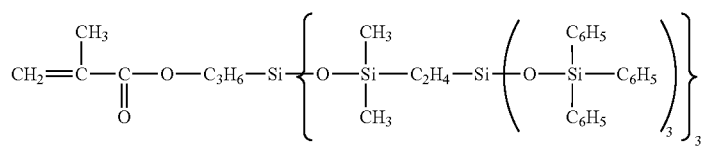

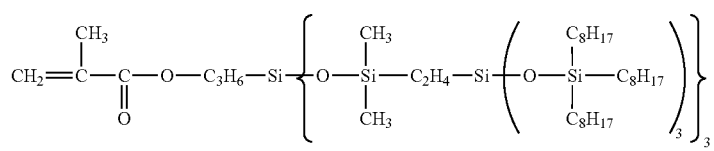

-continued
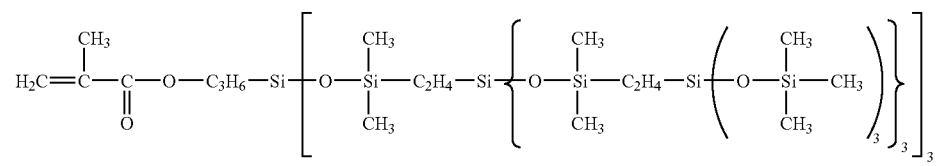
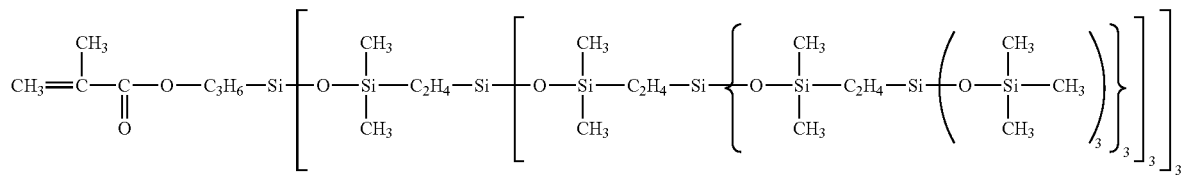
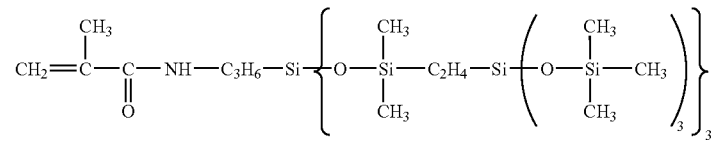
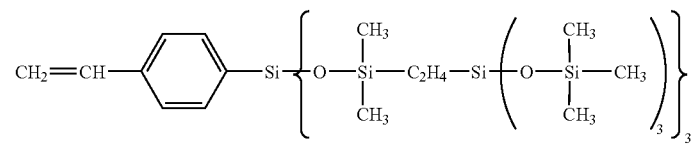
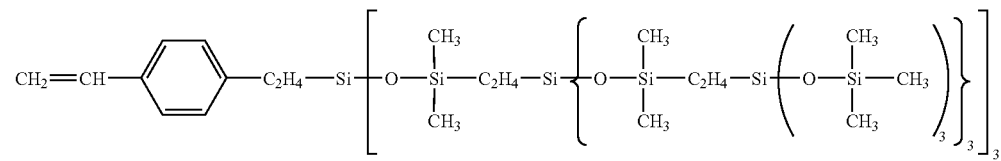
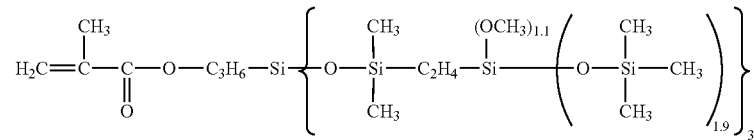
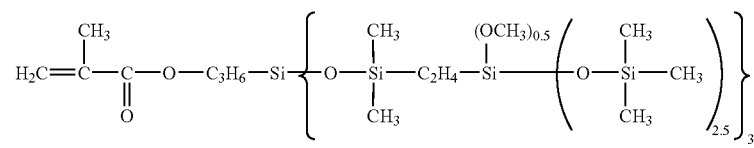
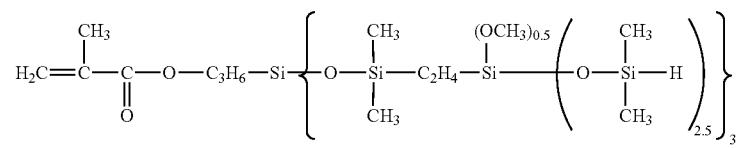
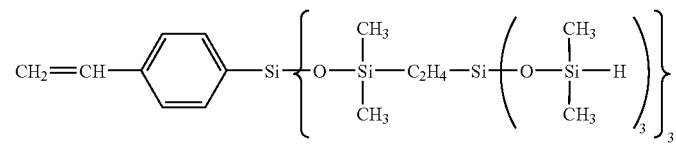
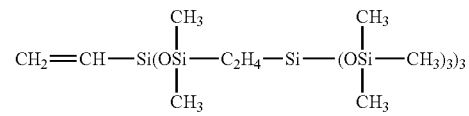
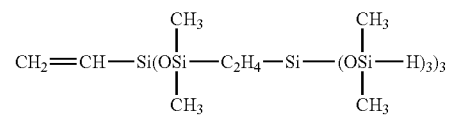

In at least one embodiment, the carbosiloxane dendrimers of the component (C) may be prepared using the method of preparation for branched siloxane/silylakylene copolymers described, for example, in European Patent No. 1 055 674. For example, they may be prepared by subjecting alkenyl-containing organic silicone compounds and silicone compounds comprising hydrogen atoms bonded to silicon, represented by the formula:

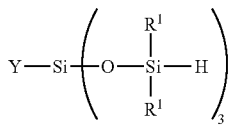

(wherein $R^1$ and Y are defined above) to a hydrosilation reaction. Examples of silicon compounds of the above formula include, but are not limited to, 3-methacryloxypropyltris(dimethylsiloxy)silane, 3-acryloxypropyltris(dimethylsiloxy)silane, and 4-vinylphenyltris(dimethylsiloxy)silane. Vinyltris(trimethylsiloxy)silane, vinyltris(dimethylphenylsiloxy)silane, and 5-hexenyltris(trimethylsiloxy)silane may be used as alkenyl-containing organic silicon compounds in at least one embodiment. In another embodiment, the hydrosilation reaction may be carried out in the presence of a transition metal catalyst such as chloroplatinic acid and the platinum/vinylsiloxane complex.

The copolymerization ratio of component (C), in terms of its weight ratio relative to the total weight of compound (A) and of compound (B), may range, for example, from 0.1:99.9 to 99.9:0.1, such as from 1:99 to 99:1, or from 5:95 to 95:5.

Amino groups may be introduced into the side chains of the vinyl polymer by including, in component (B), vinyl monomers containing amino groups, such as dimethyl-aminoethyl acrylate, dimethylaminoethyl methacrylate, diethylaminoethyl acrylate, and diethylaminoethyl methacrylate, and then carrying out a modification with potassium monochloride acetate, ammonium monochloride acetate, aminomethylpropanol salt of monochloroacetic acid, triethanolamine salt of monobromoacetic acid, sodium monochloropropionate, and other alkali metal salts of halogenated fatty acids. It is possible to introduce carboxylic acid groups into the side chains of the vinyl polymer by including, in the component (B), vinyl monomers containing carboxylic acids, such as acrylic acid, methacrylic acid, itaconic acid, crotonic acid, fumaric acid, maleic acid and the like, and then neutralizing the product with triethylamine, diethylamine, triethanolamine, and other amines.

The fluorinated vinyl polymer may be chosen, for example, from the polymers described in the examples of International Patent Application Publication No. WO 03/045337.

According to one embodiment, the graft vinyl polymers for the purposes of the present invention may be carried in an oil, for example, a volatile oil, chosen from silicone oils and/or hydrocarbon oils.

According to another embodiment, the silicone oil may be cyclopentasiloxane.

According to yet another embodiment, the hydrocarbon oil may be isododecane.

The vinyl polymers grafted with at least one carbosiloxane dendrimer-derived unit which may be used in accordance with the present disclosure include, but are not limited to, the polymers sold under the names TIB 4-100, TIB 4-101, TIB 4-120, TIB 4-130, TIB 4-200, FA 4002 ID (TIB 4-202), TIB 4-220, and FA 4001 CM (TIB 4-230) by the company Dow Corning.

The vinyl polymer having at least one unit derived from a carbosiloxane dendrimer may be present in an amount, as active material, ranging from 0.1% to 30% by weight, relative to the total weight of the composition, for example, from 0.5% to 20% by weight, from 1% to 10% by weight, or from 2% to 7% by weight.

Olefin Copolymer

The composition according to the present disclosure comprises at least one olefin copolymer chosen from amorphous olefin copolymers and olefin copolymers with controlled and moderate crystallization.

As used herein, the expression "olefin copolymer" is understood to mean any copolymer formed by polymerization of at least one olefin and another additional monomer different from the at least one olefin.

The olefin may be, in at least one embodiment, an ethylenically unsaturated monomer.

Non-limiting examples of olefins include ethylene hydrocarbon monomers comprising, for instance, one or two ethylene unsaturations, and comprising from 2 to 5 carbon atoms, such as ethylene, propylene, butadiene, and isoprene.

Amorphous Olefin Copolymer

According to one embodiment, the olefin copolymer may be an amorphous copolymer formed by polymerization of at least one olefin.

As used herein, the expression "amorphous copolymer" is understood to mean a polymer which does not have a crystalline form. The amorphous copolymer is also film-forming, that is to say it is capable of forming a film during its application to the skin.

The amorphous olefin copolymer may be chosen, for instance, from diblock, triblock, multiblock, radial, and star-shaped copolymers, and mixtures thereof.

Such amorphous olefin copolymers are described, for example, in U.S. Patent Application Publication No. 2002/005562 and U.S. Pat. No. 5,221,534.

In at least one embodiment, the amorphous olefin copolymer is an amorphous styrene and olefin block copolymer.

In another embodiment, the amorphous olefin copolymer is hydrogenated in order to reduce the residual ethylene unsaturations after polymerization of the monomers.

In yet another embodiment, the amorphous olefin copolymer is an optionally hydrogenated copolymer having styrene blocks and having ethylene/$C_3$-$C_4$ alkylene blocks.

Examples of optionally hydrogenated diblock copolymers include, but are not limited to, styrene-ethylene/propylene copolymers and styrene-ethylene/butadiene copolymers. Diblock polymers are sold, for example, under the name Kraton® G1701E by the company Kraton Polymers.

Examples of optionally hydrogenated triblock copolymers include, but are not limited to, styrene-ethylene/propylene-styrene copolymers, styrene-ethylene/butadiene-styrene copolymers, styrene-isoprene-styrene copolymers, and styrene-butadiene-styrene copolymers. Triblock polymers are sold, for example, under the names Kraton® G1650, Kraton® G1652, Kraton® D1101, Kraton® D1102, and Kraton® D1160 by the company Kraton Polymers.

It is also possible to use a mixture of hydrogenated styrene-butylene/ethylene-styrene triblock copolymer and hydrogenated ethylene-propylene-styrene star-shaped polymer, such as the mixture in isododecane. Such mixtures are sold, for example, by the company PENRECO under the trade names VERSAGEL® M5960 and VERSAGEL® M5670.

According to one embodiment, the amorphous olefin copolymer is a diblock copolymer, such as those described above, for instance, a styrene-ethylene/propylene diblock copolymer.

Olefin Copolymer with Controlled and Moderate Crystallization

According to another embodiment, the olefin copolymer is an olefin copolymer with controlled and moderate crystallization.

The olefin copolymers with controlled and moderate crystallization used in the composition of the present disclosure may be any olefin copolymer, such as a copolymer comprising solely olefin units, having a controlled and moderate crystalline character, that is to say, a level of crystallinity at most equal to 50%, for example, ranging from 5 to 40%, or from 10 to 35%.

These copolymers are generally elastomers or plastomers and may be synthesized by any process known in the art, for instance, by the free radical route, by Ziegler-Natta catalysis, or by metallocene catalysis. Such polymers are described, for example, in European Patent Application No. 1 034 776.

Examples of a first class of olefin copolymers with controlled and moderate crystallization, which can be used in the compositions according to the present disclosure, include copolymers of linear or branched α-olefins, such as $C_2$-$C_{16}$, for instance, $C_2$-$C_{12}$, α-olefins. According to one embodiment, these copolymers are bi- or terpolymers, for example, bipolymers.

Bipolymers suitable for the compositions of the present disclosure include, but are not limited to, bipolymers of ethylene and $C_4$-$C_{16}$, such as $C_4$-$C_{12}$, α-olefins and bipolymers of propylene and $C_4$-$C_{16}$, such as $C_4$-$C_{12}$, α-olefins. In at least one embodiment, the α-olefin is chosen from 1-butene, 1-pentene, 1-hexene, 1-octene, 1-nonene, 1-decene, 1-undecene, 1-dodecene, 3,5,5-trimethyl-1-hexene, 3-methyl-1-pentene, and 4-methyl-1-pentene.

According to another embodiment, the a-olefin is chosen from 1-butene and 1-octene.

In another embodiment, the bipolymers may be chosen from elastomers having a level of crystallinity ranging from 10 to 35%.

According to a further embodiment, the bipolymers may be synthesized by metallocene catalysis.

Such bipolymers are marketed, for instance, by the company DOW CHEMICAL under the trade names "AFFINITY" (plastomers) and by the company Dupont de Nemours under the name "ENGAGE" (elastomers).

Ethylene-butene bipolymers are marketed, for example, by the company EXXON under the trade name "EXACT RESINS" and by the company ELENAC under the trade name "LUFLEXEN".

Non-limiting examples of terpolymers include terpolymers of ethylene, propylene, and $C_4$-$C_{16}$, such as $C_4$-$C_{12}$, α-olefins.

In at least one embodiment, in these terpolymers, the $C_4$-$C_{16}$ α-olefin contents are as indicated above and the α-olefins may be chosen, for example, from butene, hexane, and octene.

According to another embodiment, the copolymers may be chosen from those described in the European Patent Application No. 1 034 776, such as ethylene/octene copolymers sold under the reference "Engage 8400" by the company Dupont de Nemours.

A second class of olefin copolymers with controlled and moderate crystallization suitable for use in accordance with the present disclosure include copolymers of ethylene and/or propylene and a cycloolefin, such as bipolymers.

In at least one embodiment, the cycloolefin content of the copolymers may be less than 20 mol %.

Suitable cycloolefins which can be used in accordance with the present disclosure include cyclobutene, cyclohexene, cyclooctadiene, norbornene, dimethano-octahydronaphthalene (DMON), ethylidene norbornene, vinyl norbornene, and 4-vinylcyclohexene.

In at least one embodiment, the copolymers of this class may be copolymers of ethylene and norbornene. The norbornene content of these copolymers may be, for example, less than 18 mol % in order to exhibit a crystalline character and these copolymers may be synthesized by metallocene catalysis.

Suitable ethylene/norbornene copolymers are marketed, for instance, by the companies MITSUI PETROCHEMICAL and MITSUI-SEKKA under the trade name "APPEL" and by the company HOECHST-CELANESE under the trade name "TOPAS".

Other examples of suitable ethylene/cycloolefin copolymers include, but are not limited to, ethylene/cyclobutene and ethylene/cyclohexene bipolymers having low cycloolefin content, for instance, less than 20 mol %.

The olefin copolymers may also be chosen from copolymers of at least one monoolefin and at least one monomer with at least one ethylene bond such as dienes, for example, ethylene/butadiene, propylene/butadiene, ethylene/isoprene, and propylene/isoprene bipolymers, and ethylene/propylene/diene terpolymers, which may also obtained by metallocene synthesis.

The "ethylene" and/or "diene" units may be present in the copolymer with controlled crystallization in an amount ranging, for example, from 3 to 20 mol %.

According to one embodiment, the olefin copolymer with controlled and moderate crystallization is chosen from ethylene/octene copolymers and ethylene/norbornene copolymers.

According to another embodiment, the olefin copolymer may be a polymeric gelling agent capable of thickening or gelling the organic phase of the composition.

According to yet another embodiment, the olefin copolymer may be film-forming. As used herein, the expression "film-forming polymer" is understood to mean a polymer capable of forming, on its own or with the aid of a film-forming aid, a macroscopically continuous film on a support, for example, keratin materials, and in at least one embodiment, capable of forming a cohesive film, for instance, a film whose cohesion and mechanical properties are such that the said film may be isolated from the support.

According to a further embodiment, the olefin copolymer is chosen from amorphous olefin copolymers, for example, diblock copolymers such as those of styrene-ethylene/propylene described above.

The olefin copolymer may be present in the composition according to the present disclosure in an amount ranging from 0.1% to 10% by weight, relative to the total weight of the composition, for instance, ranging from 0.2% to 5% by weight, or from 0.5% to 3% by weight.

According to one embodiment, the composition according to the present disclosure comprises:
  at least one vinyl polymer grafted with a carbosiloxane dendrimer which is the product of polymerization of:
  (A) from 0.1 to 99 parts by weight of at least one monomer chosen from acrylate and methacrylate monomers; and
  (B) from 100 to 0.1 parts by weight of at least one monomer chosen from acrylate and methacrylate monomers of a carbosiloxane dendrimer tri[tri(trimethylsiloxy)silylethyl dimethylsiloxy]silylpropyl,
wherein the carbosiloxane dendrimer tri[tri(trimethylsiloxy)silylethyl dimethylsiloxy]silylpropyl is chosen from compounds of the following formulas:

$$CH_2=C(CH_3)-C(=O)-O-C_3H_6-Si\left\{O-Si(CH_3)-C_2H_4-Si\left(O-Si(CH_3)_2-CH_3\right)_3\right\}_3$$

$$CH_2=CH-C(=O)-O-C_3H_6-Si\left\{O-Si(CH_3)-C_2H_4-Si\left(O-Si(CH_3)_2-CH_3\right)_3\right\}_3$$

and,
  at least one olefin copolymer chosen from amorphous olefin copolymers, for example, diblock copolymers such as those of styrene-ethylene/propylene described above.

Fatty Phase

The composition according to the present disclosure further comprises a liquid fatty phase.

The liquid fatty phase comprises at least one oil chosen from volatile oils, non-volatile oils, and mixtures thereof.

According to one embodiment, the composition according to the present disclosure may comprise at least one volatile oil.

As used herein, the expression "volatile oil" is understood to mean any oil capable of evaporating upon contact with the skin, at room temperature and atmospheric pressure. The volatile oils of the invention are volatile cosmetic oils, which are liquid at room temperature and which have a vapor pressure which is not zero, at room temperature and atmospheric pressure, ranging, for example, from 0.13 Pa to 40 000 Pa (0.001 to 300 mmHg), such as from 1.3 to 1300 Pa (0.01 to 10 mmHg).

The volatile oil may be chosen from volatile hydrocarbon oils, volatile silicone oils, volatile fluorinated oils, and mixtures thereof.

According to one embodiment, the composition according to the present disclosure may comprise at least one volatile hydrocarbon oil.

As used herein, the expression "hydrocarbon oil" is understood to mean an oil comprising mainly hydrogen and carbon atoms and optionally at least one atom chosen from oxygen, nitrogen, sulphur, and/or phosphorus atoms.

The volatile hydrocarbon oils may be chosen from hydrocarbon oils comprising from 8 to 16 carbon atoms, for example, branched $C_8$-$C_{16}$ alkanes such as $C_8$-$C_{16}$ isoalkanes of petroleum origin (also called isoparaffins) such as isododecane (also called 2,2,4,4,6-pentamethylheptane), isodecane, isohexadecane, and, for example, the oils sold under the trade names Isopars® and Permethyls®.

Other examples of suitable volatile oils include, but are not limited to, volatile silicones such as linear and cyclic volatile silicone oils, for example, those having a viscosity≤5 centistokes ($5 \times 10^{-6}$ m$^2$/s), and comprising, for instance, from 2 to 10 silicon atoms, such as from 2 to 7 silicon atoms, these silicones optionally comprising at least one group chosen from alkyl and alkoxy groups comprising from 1 to 10 carbon atoms. Non-limiting examples of such volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyidisiloxane, octamethyltrisiloxane, decamethyltetrasiloxane, dodecamethylpentasiloxane, and mixtures thereof.

In at least one embodiment, the volatile fluorinated oil has no flash point.

Examples of volatile fluorinated oils include, but are not limited to, nonafluoroethoxybutane, nonafluoromethoxybutane, decafluoropentane, tetradecafluorohexane, dodecafluoropentane, and mixtures thereof.

According to one embodiment, the composition according to the present disclosure may comprise at least two different volatile oils, for instance, at least three different volatile oils.

For example, the composition according to the present disclosure may comprise isododecane, cyclopentasiloxane, isohexadecane, and mixtures thereof.

The composition according to the present disclosure may comprise a volatile oil in an amount ranging from 1 to 80% by weight relative to the total weight of the composition, for example, from 5 to 70% by weight, from 10 to 60% by weight, or from 15 to 50% by weight.

The composition according to the present disclosure may comprise at least one non-volatile oil.

As used herein, the expression "non-volatile oil" is understood to mean an oil which remains on the skin at room temperature and atmospheric pressure for at least several hours and which has, for example, a vapor pressure of less than 0.13 Pa (0.01 mmHg).

These non-volatile oils may be hydrocarbon oils such as hydrocarbon oils of animal and plant origin, silicone oils, and mixtures thereof. As used herein, the expression "hydrocarbon oil" is understood to mean an oil comprising mainly hydrogen and carbon atoms and optionally at least one atom chosen from oxygen, nitrogen, sulphur, and/or phosphorus atoms.

The non-volatile oils may be chosen, for example, from non-volatile hydrocarbon oils, which may be optionally fluorinated, and/or silicone oils.

Non-limiting examples of non-volatile hydrocarbon oil include:

hydrocarbon oils of animal origin, hydrocarbon oils of plant origin such as triglycerides comprising fatty acid esters of glycerol in which the fatty acids may have varied chain lengths ranging from $C_4$ to $C_{24}$, it being possible for these chains to be linear or branched, saturated or unsaturated; for example, triglycerides of heptanoic acid and octanoic acid; triglycerides of wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, lucerne oil, poppy seed oil, pumpkin seed oil, sesame oil, gourd oil, blackcurrant oil, evening primrose oil, millet oil, barley oil, quinoa oil, rye oil, safflower oil, candlenut oil, passion flower oil, and musk rose oil; shea butter; and triglycerides of caprylic/capric acids such as those sold by the company Stearineries Dubois or those sold under the names Miglyol 810®, 812®, and 818® by the company Dynamit Nobel, synthetic ethers comprising from 10 to 40 carbon atoms;

linear or branched hydrocarbons of mineral or synthetic origin such as petroleum jelly, polydecenes, hydrogenated polyisobutene such as Parleam®, squalane, paraffin oils, and mixtures thereof, synthetic esters such as oils of formula $R_1COOR_2$ wherein $R_1$ is a residue of a linear or branched fatty acid comprising from 1 to 40 carbon atoms and $R_2$ is chosen from hydrocarbon, such as branched hydrocarbon, chains comprising from 1 to 40 carbon atoms, with the proviso that the number of carbon atoms in $R_1+R_2$ is ≥10, for example, Purcellin oil (cetostearyl octanoate), isopropyl myristate, isopropyl palmitate, $C_{12}$ to $C_{15}$ alcohol benzoates, hexyl laurate, diisopropyl adipate, isononyl isononanoate, isodecyl neopentanoate, 2-ethylhexyl palmitate, isostearyl isostearate, 2-hexyldecyl laurate, 2-octyldecyl palmitate, 2-octyldodecyl myristate, alcohol and polyalcohol heptanoates, octanoates, decanoates, and ricinoleates such as propylene glycol dioctanoate; hydroxylated esters such as isostearyl lactate, diisostearyl malate, 2-octyldodecyl lactate; polyol esters, and pentaerythritol esters, fatty alcohols which are liquid at room temperature and which comprise a branched and/or unsaturated carbon chain comprising from 12 to 26 carbon atoms such as octyldodecanol, isostearyl alcohol, oleyl alcohol, 2-hexyldecanol, 2-butyloctanol, and 2-undecylpentadecanol, and higher fatty acids such as oleic acid, linoleic acid, linolenic acid, and mixtures thereof.

Other examples of non-volatile silicone oils which can be used in the composition according to the present disclosure include, but are not limited to, non-volatile polydimethylsiloxanes (PDMS), polydimethylsiloxanes comprising alkyl and/or alkoxy groups which are pendant and/or at the silicone chain ends, these groups each comprising from 2 to 24 carbon atoms, phenylated silicones such as phenyl trimethicones, phenyl dimethicones, phenyltrimethylsiloxydiphenylsiloxanes, diphenyl dimethicones, and diphenylmethyldiphenyltrisiloxanes, and mixtures thereof.

The non-volatile oil may be present in the composition according to the present disclosure in an amount ranging from 0.5% to 80% by weight, relative to the total weight of the composition, for example, from 1% to 50% by weight, or from 2% to 30% by weight.

The liquid fatty phase may be present in the composition according to the present disclosure in a total amount ranging from 1 to 90% by weight relative to the total weight of the composition, for example, from 5 to 80% by weight, from 10 to 70% by weight, or from 25 to 60% by weight.

The fatty phase of the composition according to the present disclosure may also comprise fatty substances other than the oils mentioned above, such as waxes and pasty fatty substances.

As used herein, the expression "waxes" is understood to mean a fatty substance which is solid at room temperature.

It is possible to define pasty fatty substances with the aid of at least one of the following physicochemical properties:
a viscosity ranging from 0.1 to 40 Pa·s (1 to 400 poises), measured at 40° C. with a CONTRAVES TV rotational viscometer equipped with an MS-r3 or MS-r4 rotor at the frequency of 60 Hz, and/or
a melting point ranging from 25-70° C., for instance, from 25-55° C.

Examples of waxes which can be used according to the present disclosure include, but are not limited to:
waxes of animal origin such as beeswax, spermaceti, lanolin wax and lanolin derivatives, vegetable waxes such as Carnauba wax, Candelilla wax, Ouricury wax, Japan wax, cocoa butter, sugar cane waxes, and cork fiber waxes,
mineral waxes, for example, paraffin, petroleum jelly, lignite, microcrystalline waxes, and ozokerites,
synthetic waxes such as polyethylene waxes and waxes obtained by Fisher-Tropsch synthesis,
silicone waxes, for instance, substituted linear polysiloxanes; such as polyether silicone waxes, alkyl and alkoxy-dimethicones comprising from 16 to 45 carbon atoms, alkyl methicones such as $C_{30}$-$C_{45}$ alkyl methicone sold under the trade name "AMS C 30" by DOW CORNING,
hydrogenated oils which are solid at 25° C., such as hydrogenated castor oil, hydrogenated jojoba oil, hydrogenated palm oil, hydrogenated tallow, and hydrogenated coconut oil, and fatty acids which are solid at 25° C., such as $C_{20}$-$C_{40}$ alkyl stearate sold under the trade name "KESTER WAX K82H" by the company KOSTER KEUNEN,
and mixtures thereof.

According to one embodiment, the at least one wax is chosen from polyethylene waxes, microcrystalline waxes, carnauba waxes, hydrogenated jojoba oil, candelilla waxes, beeswaxes, and/or mixtures thereof.

The at least one wax may be present in the composition in an amount ranging from 0.1 to 30% by weight, for example, from 0.5 to 20% by weight, relative to the total weight of the composition.

The fatty substances may be chosen in various ways by persons skilled in the art so as to prepare a composition having the desired properties, for example, in terms of consistency and/or texture.

Thickening Agent

The composition according to the present disclosure may further comprise, in addition to the at least one olefin copolymer, at least one thickening agent for oils which may be chosen from polymeric thickening agents, inorganic thickening agents, and mixtures thereof.

The polymeric thickening agent for oils is capable of thickening and/or gelling the organic phase of the composition. The polymeric thickening agent may also be film-forming, that is to say, capable of forming a film during its application to the skin.

The polymeric thickening agent for oils may be chosen, for example, from:
polyamide-type polycondensates resulting from the condensation between (α) at least one acid chosen from dicarboxylic acids comprising at least 32 carbon atoms such as dimeric fatty acids and (β) at least one alkylenediamine, such as ethylenediamine, in which the polyamide polymer comprises at least one terminal carboxylic acid group esterified or amidated with at least one monoalcohol and/or at least one monoamine comprising from 12 to 30 linear and/or saturated carbon atoms, for example, ethylenediamine/stearyl dilinoleate copolymers such as those marketed under the name Uniclear 100 VG® by the company ARIZONA CHEMICAL;
silicone polymers chosen from:
1) polyorganosiloxanes comprising at least two groups capable of establishing hydrogen interactions, these two groups being located in the polymer chain, and/or
2) polyorganosiloxanes comprising at least two groups capable of establishing hydrogen interactions, these two groups being located on grafts and/or branches.

The groups capable of establishing hydrogen interactions may be chosen, for instance, from ester, amide, sulphonamide, carbamate, thiocarbamate, urea, urethane, thiourea, oxamido, guanidine, and biguanidino groups, and mixtures thereof.

Silicone polymers which may be used as structuring agents in the composition of the present disclosure include, but are not limited to, polyorganosiloxane-type polymers, for example, those described in U.S. Pat. Nos. 5,874,069, 5,919, 441, 6,051,216, and 5,981,680.

In at least one embodiment, the silicone polymers are polyorganosiloxanes as defined above in which the units capable of establishing hydrogen interactions are present in the polymer chain.

The silicone polymers may be chosen, for example, from polymers comprising at least one unit of formula (I):

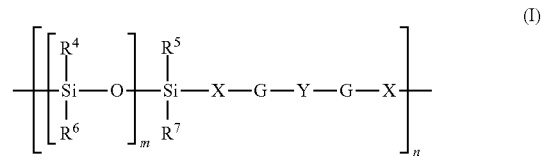

wherein:
1) $R^4$, $R^5$, $R^6$, and $R^7$, which may be identical or different, are groups chosen from:
saturated or unsaturated, linear, branched, or cyclic $C_1$ to $C_{40}$ hydrocarbon groups optionally comprising in their chain at least one atom chosen from oxygen, sulphur, and/or nitrogen atoms, and which may be partly or completely substituted with fluorine atoms,
$C_6$ to $C_{10}$ aryl groups which are optionally substituted with at least one $C_1$ to $C_4$ alkyl groups,
polyorganosiloxane chains optionally comprising at least one atom chosen from oxygen, sulphur, and/or nitrogen atoms,
2) the groups X, which may be identical or different, are chosen from linear or branched $C_1$ to $C_{30}$ alkylenediyl groups which may comprise in their chains at least one atom chosen from oxygen and/or nitrogen atoms,
3) Y is chosen from linear or branched divalent alkylene groups, arylene groups, cycloalkylene groups, alkylarylene groups, and arylalkylene groups, which may be saturated or unsaturated $C_1$ to $C_{50}$ groups optionally comprising at least one atom chosen from oxygen, sulphur, and/or nitrogen atoms, and/or which may carry, as substituent, at least one substituent chosen from fluorine, hydroxy groups, $C_3$ to $C_8$ cycloalkyl groups, $C_1$ to $C_{40}$ alkyl groups, $C_5$ to $C_{10}$ aryl groups, phenyl groups optionally substituted with 1 to 3 $C_1$ to $C_3$ alkyl groups, $C_1$ to $C_3$ hydroxyalkyl groups, and $C_1$ to $C_6$ aminoalkyl groups, or 4) Y is a group of the following formula:

$$R^8-T\begin{matrix}\diagup\\ \diagdown\end{matrix}$$

wherein:
- T is chosen from saturated or unsaturated, linear or branched, trivalent or tetravalent $C_3$ to $C_{24}$ hydrocarbon groups optionally substituted with a polyorganosiloxane chain, and which may comprise at least one atom chosen from O, N, and S, or T is a trivalent atom chosen from N, P, and Al, and
- $R^8$ is chosen from linear or branched $C_1$ to $C_{50}$ alkyl groups and polyorganosiloxane chains, which may comprise at least one group chosen from ester, amide, urethane, thiocarbamate, urea, thiourea, and/or sulphonamide groups, which may or may not be linked to another chain of the polymer,
5) the G groups, which may be identical or different, are divalent groups chosen from:

$$-\underset{\underset{O}{\parallel}}{C}-O-;\quad -O-\underset{\underset{O}{\parallel}}{C}-;\quad -N(R^9)-\underset{\underset{O}{\parallel}}{C}-;$$
$$-\underset{\underset{O}{\parallel}}{C}-N(R^9)-;\quad -N(R^9)-SO_2-;$$
$$-SO_2-N(R^9)-;\quad -N(R^9)-\underset{\underset{O}{\parallel}}{C}-O-;$$
$$-O-\underset{\underset{O}{\parallel}}{C}-N(R^9)-;\quad -N(R^9)-\underset{\underset{S}{\parallel}}{C}-O-;$$
$$-O-\underset{\underset{S}{\parallel}}{C}-N(R^9)-;\quad -N(R^9)-\underset{\underset{O}{\parallel}}{C}-N(R^9)-;$$
$$-N(R^9)-\underset{\underset{S}{\parallel}}{C}-N(R^9)-;\quad -N(R^9)-\underset{\underset{O}{\parallel}}{C}-\underset{\underset{O}{\parallel}}{C}-N(R^9);$$
$$-NH-\underset{\underset{NH}{\parallel}}{C}-NH-; \text{ and}$$
$$-NH-\underset{\underset{NH}{\parallel}}{C}-NH-\underset{\underset{NH}{\parallel}}{C}-NH-$$

wherein $R^9$ is chosen from hydrogen and linear or branched $C_1$ to $C_{20}$ alkyl groups, with the proviso that at least 50% of the $R^9$ groups of the polymer are hydrogen atom and at least two of the groups G of the polymer are a group other than:

$$-O-\underset{\underset{O}{\parallel}}{C}- \text{ and } -\underset{\underset{O}{\parallel}}{C}-O-;$$

6) is an integer ranging from 2 to 500, for example, from 2 to 200, and m is an integer ranging from 1 to 1000, for instance, from 1 to 700, or from 6 to 200.

According to one embodiment of the present disclosure, at least 80% of the $R^4$, $R^5$, $R^6$, and $R^7$ groups of the polymer may be chosen from methyl, ethyl, phenyl, and 3,3,3-trifluoropropyl groups.

According to another embodiment, the groups capable of establishing hydrogen interactions are amide groups of formula —C(O)NH— and —HN—C(O)—. In this case, the structuring agent may be a polymer comprising at least one unit chosen from units of formulas (III) and (IV):

$$\left[-\underset{\underset{O}{\parallel}}{C}-X-\left[SiO\begin{matrix}R^4\\ |\\ |\\ R^6\end{matrix}\right]_m-\underset{R^7}{\overset{R^5}{\underset{|}{Si}}}-X-\underset{\underset{O}{\parallel}}{C}-NH-Y-NH-\right]_n \quad (III)$$

$$\left[-NH-X-\left[SiO\begin{matrix}R^4\\ |\\ |\\ R^6\end{matrix}\right]_m-\underset{R^7}{\overset{R^5}{\underset{|}{Si}}}-X-NH-\underset{\underset{O}{\parallel}}{C}-Y-\underset{\underset{O}{\parallel}}{C}-\right]_n \quad (IV)$$

wherein $R^4$, $R^5$, $R^6$, $R^7$, X, y, m, and n are defined above.

In these polyamides of formulas (III) and/or (IV), m may range from 1 to 700, for instance, from 15 to 500, or from 50 to 200, and n may range from 1 to 500, for example, from 1 to 1 00, or from 4 to 25,
- X may be a linear or branched alkylene chain comprising from 1 to 30 carbon atoms, such as from 1 to 20 carbon atoms, from 5 to 15 carbon atoms, or 10 carbon atoms, and
- Y may be chosen from linear or branched alkylene chains and chains which may comprise rings and/or unsaturations, comprising from 1 to 40 carbon atoms, such as from 1 to 20 carbon atoms, from 2 to 6 carbon atoms, or 6 carbon atoms,
- galactomannans comprising from one to six, such as from two to four, hydroxyl groups per monosaccharide, substituted with a saturated or unsaturated alkyl chain, such as guar gums alkylated with $C_1$ to $C_6$, for instance, $C_1$ to $C_3$, alkyl chains, and mixtures thereof.

The composition according to the present disclosure may also comprise at least one inorganic thickening agent for oils such as organophilic clays and pyrogenic silicas.

The organophilic clays are clays modified with chemical compounds which make the clay capable of swelling in oily media.

Clays are products known in the art, and described, for example, in the book "Mineralogie des argiles, S. Caillere, S. Henin, M. Rautureau, 2nd edition 1982, Masson".

Clays are silicates containing a cation which may be chosen from calcium, magnesium, aluminium, sodium, potassium, and lithium cations, and mixtures thereof.

Non-limiting examples of such products include smectite clays such as montmorillonites, hectorites, bentonites, beidellites, saponites, vermiculites, stevensite, and chlorites.

These clays may be of natural or synthetic origin. In at least one embodiment, the clays are cosmetically compatible and acceptable with keratin materials such as the skin.

Examples of organophilic clays include, but are not limited to, montmorillonite, bentonite, hectorite, attapulgite, sepiolite, and mixtures thereof. According to one embodiment, the clay may be chosen from bentonite and hectorite.

These clays may optionally be modified with a chemical compound chosen from quaternary amines, tertiary amines, amine acetates, imidazolines, amine soaps, fatty sulphates, alkyl aryl sulphonates, amine oxides, and mixtures thereof.

Further non-limiting examples of organophilic clays include quaternium-18 bentonites such as those sold under the names BENTONE 3, BENTONE 38, and BENTONE 38V by the company Rheox, BENTONE ISD V by the company Elementis, TIXOGEL VP by the company United Catalyst, CLAYTONE 34, CLAYTONE 40, and CLAYTONE XL by the company Southern Clay; stearalkonium bentonites such as those sold under the names BENTONE 27 by the company Rheox, TIXOGEL LG by the company United Catalyst, CLAYTONE AF and CLAYTONE APA by the company Southern Clay; and quaternium-18/benzalkonium bentonites such as those sold under the names CLAYTONE HT and CLAYTONE PS by the company Southern Clay.

Pyrogenic silica may be obtained by high-temperature hydrolysis of a volatile silicon compound in an oxyhydrogen flame, which produces a finely divided silica. This process may make it possible to obtain hydrophilic silicas which have a large number of silanol groups at their surface. Such hydrophilic silicas are marketed, for example, under the names "AEROSIL 130®", "AEROSIL 200®", "AEROSIL 255®", "AEROSIL 300®", and "AEROSIL 380®" by the company Degussa, and "CAB-O-SIL HS-5®", "CAB-O-SIL EH-5®", "CAB-O-SIL LM-130®", "CAB-O-SIL MS-55®", and "CAB-O-SIL M-5®" by the company Cabot.

It is possible to chemically modify the surface of the silica by chemical reaction generating a reduction in the number of silanol groups. For instance, it is possible to replace silanol groups with hydrophobic groups to obtain a hydrophobic silica.

The hydrophobic groups may be chosen, for example, from:
- trimethylsiloxyl groups, which may be obtained by treating pyrogenic silica in the presence of hexamethyldisilazane. Silicas thus treated are called "Silica silylate" according to CTFA ($6^{th}$ edition, 1995) and are marketed, for example, under the references "AEROSIL R812®" by the company Degussa and "CAB-O-SIL TS-530®" by the company Cabot,
- dimethylsilyloxyl and polydimethylsiloxane groups, which may be obtained by treating pyrogenic silica in the presence of polydimethylsiloxane or dimethyldichlorosilane. Silicas thus treated are called "Silica dimethyl silylate" according to CTFA ($6^{th}$ edition, 1995) and are marketed, for example, under the references "AEROSIL R972®" and "AEROSIL R974®" by the company Degussa, and "CAB-O-SIL TS-610®" and "CAB-O-SIL TS-720®" by the company Cabot.

According to one embodiment, the pyrogenic silica may have a particle size in the nanometer to micrometer range, for example, ranging from about 5 to 200 nm.

In another embodiment, the composition according to the present disclosure may comprise an association of hydrophocic pyrogenic silica and quaternium-18 bentonites.

The at least one thickening agent for oils may be present in the composition according to the present disclosure in an amount, as active material, ranging from 0.01% to 15% by weight, relative to the total weight of the composition, for example, from 0.1% to 10% by weight, or from 0.3% to 5% by weight.

Aqueous Phase

The composition according to the invention may further comprise an aqueous phase.

The aqueous phase comprises water. The water may be floral water such as cornflower water and/or mineral water such as VITTEL water, LUCAS water, and LA ROCHE POSAY water, and/or thermal water.

The aqueous phase may also comprise at least one organic solvent which is miscible with water (at room temperature −25° C.), for example, monoalcohols comprising from 2 to 6 carbon atoms such as ethanol and isopropanol; polyols comprising from 2 to 20 carbon atoms, for instance, from 2 to 10 carbon atoms, or from 2 to 6 carbon atoms, such as glycerol, propylene glycol, butylene glycol, pentylene glycol, hexylene glycol, dipropylene glycol, and diethylene glycol; glycol ethers (comprising, for example, from 3 to 16 carbon atoms) such as mono-, di-, and tripropylene glycol ($C_1$-$C_4$)alkyl ethers, mono, di-, and triethylene glycol ($C_1$-$C_4$)alkyl ethers, caprylyl glycol, and mixtures thereof.

The aqueous phase may additionally comprise at least one stabilizing agent, for example, sodium chloride, magnesium dichloride, and magnesium sulphate.

The aqueous phase may also comprise at least one water-soluble or water-dispersible compound which is compatible with the aqueous phase, such as gelling agents, film-forming polymers, thickeners, surfactants, and mixtures thereof.

The aqueous phase may be present in the composition according to the present disclosure in an amount ranging from 1 to 80% by weight, relative to the total weight of the composition, for example, from 5 to 50% by weight, or from 5 to 40% by weight.

Pulverulent Phase

The composition according to the invention may further comprise a pulverulent phase, such as pigments, fillers, and/or pearlescent agents and mixtures thereof.

According to one embodiment, the composition according to the invention may comprise at least one pigment.

As used herein, the expression "pigments" is understood to mean inorganic or organic particles which are insoluble in the liquid organic phase, intended to color and/or opacify the composition.

The at least one pigment may be chosen from inorganic and organic pigments. Non-limiting examples of pigments include metal oxides such as iron oxides (for example, those which are yellow, red, brown, or black in color), titanium dioxides, cerium oxide, zirconium oxide, chromium oxide; manganese violet, ultramarine blue, Prussian blue, ultramarine blue, ferric blue, and mixtures thereof.

According to at least one embodiment, the pigments are chosen from iron oxide and/or titanium dioxide pigments.

The pigments may optionally be treated with a hydrophobic agent in order to make them compatible with the organic phase of the composition. The hydrophobic treatment agent may be chosen from silicones such as methicones, dimethicones, and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyoxides of hexafluoropropylene, polyorganosiloxanes comprising perfluoroalkyl groups, perfluoropolyethers, amino acids; N-acylated amino acids and salts thereof; lecithin, isopropyl triisostearyl titanate, and mixtures thereof.

The N-acylated amino acids may comprise an acyl group comprising from 8 to 22 carbon atoms, for example, 2-ethylhexanoyl, caproyl, lauroyl, myristoyl, palmitoyl, stearoyl, and cocoyl group. The salts of these compounds may be chosen from aluminium, magnesium, calcium, zirconium, zinc, sodium, and potassium salts. The amino acid may be chosen, for example, from lysine, glutamic acid, and alanine.

The term "alkyl" mentioned in the compounds described above means an alkyl group comprising, for example, from 1 to 30 carbon atoms, such as from 5 to 16 carbon atoms.

Suitable hydrophobic treated pigments are described, for instance, in European Patent Application No. 1 086 683.

The at least one pigment may be present in the composition according to the present disclosure in an amount ranging from 0.1 to 40% by weight, relative to the total weight of the composition, for example, from 1% to 30% by weight, or from 5% to 15% by weight.

In addition to the pigments, the pulverulent phase of the composition according to the present disclosure may comprise fillers and/or pearlescent agents.

According to one embodiment, the composition according to the present disclosure may comprise at least one filler.

As used herein, the expression "fillers" is understood to mean colorless or white, mineral or synthetic particles of any shape, which are insoluble in the medium of the composition regardless of the temperature at which the composition is manufactured.

The at least one filler may be chosen from platelet, spherical, or oblong, inorganic or organic fillers of any shape, regardless of the crystallographic shape (for example sheet, cubic, hexagonal, orthorhombic, and the like). Examples of suitable fillers include, but are not limited to, talc, mica, silica, kaolin, polyamide powders (Nylon®), poly-β-alanine powders, polyethylene powders, polymethyl methacrylates, polyurethane powders such as the hexamethylene diisocyanate and trimethylol hexyl lactone copolymer powder sold under the names PLASTIC POWDER D-400 by the company TOSHIKI, tetrafluoroethylene polymer powders (Teflon®), micronized wax particles, for instance, Carnauba microwaxes such as those marketed under the name "MicroCare 350®" by the company MICRO POWDERS, synthetic wax microwaxes such as those marketed under the name "MicroEase 114S®" by the company MICRO POWDERS, microwaxes comprising a mixture of Carnauba wax and polyethylene wax such as those marketed under the names "MicroCare 300®" and "310®" by the company MICRO POWDERS, microwaxes comprising of a mixture of Carnauba wax and synthetic wax such as those marketed under the name "MicroCare 325®" by the company MICRO POWDERS, polyethylene microwaxes such as those marketed under the names "MicroPoly 200®", "220®", "220L®", and "250S®", by the company MICRO POWDERS, and those marketed under the name "CERAPURE H5-C" by the company SHAMROCK, polypropylene microwaxes such as those marketed under the name "MATTEWAX" by the company MICRO POWDERS; lauroyl lysine, starch, boron nitride, hollow polymer microspheres such as those of polyvinylidene chloride/acrylonitrile such as Expancel® (Nobel Industrie), acrylic acid copolymers, silicone resin powders, for example, silsesquioxane powders (silicone resin powders described, for instance, in European Patent No. 0 293 795; for example, Tospearls® from Toshiba), elastomeric polyorganosiloxane particles, precipitated calcium carbonate, magnesium carbonate and hydrocarbonate, hydroxyapatite, hollow silica microspheres, glass and ceramic microcapsules, metal soaps derived from organic carboxylic acids comprising from 8 to 22 carbon atoms, such as from 12 to 18 carbon atoms, for example zinc, magnesium, and lithium stearate, zinc laurate, magnesium myristate; barium sulphate, and mixtures thereof.

According to one embodiment, the composition according to the present disclosure may comprise polytetrafluoroethylene (PTFE) powders, polyamide powders (Nylon®), and/or mixtures thereof.

The at least one filler may be present in the composition according to the present disclosure in a total amount ranging from 0.1% to 30% by weight, relative to the total weight of the composition, for example, from 0.5% to 20% by weight, or from 0.8% to 10% by weight.

In addition to the pigments and fillers, the particulate phase of the composition according to the present disclosure may comprise at least one pearlescent agent.

As used herein, the expression "pearlescent agents" is understood to mean iridescent particles, for example, those produced by certain molluscs in their shell or synthesized, which are insoluble in the medium of the composition.

The at least one pearlescent agent may be chosen from white pearlescent pigments such as bismuth oxychloride, mica coated with titanium, mica coated with bismuth oxychloride, colored pearlescent pigments such as mica-titanium with iron oxides, mica-titanium with ferric blue and/or chromium oxide, mica-titanium with an organic pigment of the aforementioned type, and pearlescent pigments based on bismuth oxychloride.

Additional Colorants

The composition according to the invention may comprise at least one additional colorant chosen from water-soluble and fat-soluble colorants.

The water-soluble colorants may be chosen, for example, from beet juice, methylene blue, and caramel.

As used herein, the expression "fat-soluble colorants" is understood to mean generally organic compounds which are soluble in fatty substances such as oils.

The fat-soluble colorants may include, for example, Sudan red, D&C Red No. 17, D&C Green No. 6, β-carotene, soybean oil, Sudan brown, D&C Yellow No. 11, D&C Violet No. 2, D&C Orange No. 5, quinoline yellow, annatto, and bromo acids.

Galenics

The composition according to the present disclosure may be provided in various galenic forms, for example, anhydrous forms, water-in-oil emulsions, oil-in-water emulsions, and multiple emulsions, gels, creams, suspensions, compacts, hot pours, and sticks.

The present invention may also be provided in the form of a make-up and/or care kit for keratin materials comprising at least a first composition according to the present disclosure comprising i) at least one vinyl polymer comprising at least one carbosiloxane dendrimer-derived unit and, ii) at least one olefin copolymer, and at least a second cosmetic composition.

The kit may comprise two distinct compositions intended to be applied one over the other, one of the compositions comprising at least one vinyl polymer comprising at least one carbosiloxane dendrimer-derived unit and the other composition comprising at least one olefin copolymer.

According to one embodiment, the composition according to the present disclosure may be provided in a form chosen from anhydrous forms and emulsions, such as a water-in-oil emulsion.

Additional Customary Cosmetic Ingredients

The composition according to the present disclosure may comprise at least one other customary cosmetic ingredient which may be chosen from antioxidants, perfumes, preservatives, neutralizing agents, surfactants, sunscreens, vitamins, moisturizing agents, self-tanning compounds, anti-wrinkle actives, emollients, hydrophilic and lipophilic actives, anti-free radical agents, deodorant agents, sequestrants, film-forming agents, and mixtures thereof.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

Examples 1 to 7

Seven foundations were prepared in the form of a water-in-oil emulsion having the following general formula:

| | | % by mass |
|---|---|---|
| A1 | Oxyethylenated/oxypropylenated alpha-omega polydimethylsiloxane in cyclopentasiloxane sold under the name Abil EM 97 by the company Goldschmidt | 1.80 |
| | Isostearyl diglyceryl succinate | 0.60 |
| | Butyl paraben | 0.25 |
| | Isododecane | X |
| A2 | Isododecane | 15.35 |
| | Styrene-ethylene/propylene block copolymer sold under the reference KRATON G1701E by the company Kraton Polymers | Z |
| A3 | Cyclopentasiloxane | 5.00 |
| | Iron oxides coated with aluminium stearoyl glutamate | 3.2 |
| | Titanium dioxide coated with aluminium stearoyl glutamate | 6.8 |
| A4 | Polytetrafluoroethylene (PTFE) powder | 1.4 |
| | Nylon 12 powder | 1.1 |
| B | Demineralized water | 25.25 |
| | 1-2-octane diol | 0.3 |
| | Glycerol | 3.0 |
| | Preservatives | 0.75 |
| | Magnesium sulphate | 0.70 |
| C | Vinyl copolymer containing dendritic silicone side chains in isododecane sold under the name FA 4002 ID by the company Dow Corning. | Y |
| D | Modified magnesium silicate in isododecane sold under the name Bentone Gel ISD V by the company Elementis | 8.00 |
| | TOTAL | 100% |

The foundations of Examples 1, 2, 5, 6 and 7 are foundations according to the present disclosure and the foundations of Examples 3 and 4 are for comparison since they are free of vinyl polymer having a carbosiloxane dendrimer-derived unit or of olefin copolymer, respectively.

| | Ex 1 (inventive) | Ex 2 (inventive) | Ex 3 (comparative) | Ex 4 (comparative) | Ex 5 (inventive) | Ex 6 (inventive) | Ex 7 (inventive) |
|---|---|---|---|---|---|---|---|
| X (Isododecane A1) | 17.5 | 12.5 | 25.0 | 14.0 | 18.1 | 13.1 | 0.6 |
| Y (vinyl polymer with carbosiloxane dendrimer unit) | 7.5 | 12.5 | 0 | 12.5 | 7.5 | 12.5 | 25.0 |
| Z (olefin copolymer) | 1.50 | 1.50 | 1.50 | 0 | 0.90 | 0.90 | 0.90 |

Procedure:

1. Preparation of the Phases:

Preparation of A1: The first three constituents were weighed and the mixture was heated to 75° C. so as to obtain a clear medium and then isododecane was added.

Preparation of A2: The copolymer and isododecane were mixed, with stirring (Rayneri), in a saucepan and heated to 90° C. until the medium was homogeneous.

Preparation of A3: The pigments were ground using a three-roll mill (3 rounds) in cyclopentasiloxane.

Preparation of B: The constituents were weighed and the mixture was heated until homogeneous and then left to cool to room temperature.

2. Preparation of the Emulsion:

The phases A1, A2, and A3 were introduced one after the other, with Moritz stirring, while taking care to homogenize well after addition of each of the phases and to increase the stirring rate if necessary.

The phase A4 was then added, with stirring, and then the aqueous phase B while increasing the stirring rate if necessary.

The phases C and D were then added successively and the mixture was again kept stirring for 10 minutes.

The foundations according to the present disclosure thus obtained (Examples 1, 2, 5, 6 and 7) had a fluid and soft texture and were easy to apply. The make-up obtained unified the complexion while remaining natural and without thickness, it left a comfortable deposit on the face which was soft to the touch and matte. The make-up exhibited good staying power over time for its color, its homogeneity, and its matteness. It was transfer-resistant.

Measurement of the Transfer Resistance of the Compositions of Examples 1 to 4:

The transfer resistance of the compositions of Examples 1 and 2 (according to the present disclosure) was compared to that of compositions 3 and 4 (not in accordance with the present disclosure), on a panel of 10 women.

For each subject, the area of the neck was cleaned with a non-greasy make-up remover (of the Plenitude Refreshing Eye Makeup Remover type) and left to dry in the air for 5 minutes.

0.10 to 0.15 ml of composition was applied, with a sponge, to both sides of the neck from the line delimited by the jaw up to the base of the neck.

The product was left to dry for 10 minutes.

A 24×33 cm fabric (of the Testfabrics Inc., Ref. 100% Bleached Double-Knit Interlock Cotton fabric type) was placed along the cervical collar (Soft Foam Cervical Collar type, OTC Professional Appliances) and it was attached with safety pins.

The collar was placed around the neck of the subject for 30 minutes.

The fabric was then removed and the quantity of product deposited on the fabric is visually scored using the following scale:

1=none
2=light
3=moderate
4=high

The transfer index corresponds to the mean of the scores obtained on the 10 subjects. The lower the value of this index, the less the product transfers.

Results:

|  | Ex 1 (Inventive) | Ex 2 (inventive) | Ex 3 (comparative) | Ex 4 (comparative) |
|---|---|---|---|---|
| Y (vinyl polymer with carbosiloxane dendrimer unit) | 7.5 | 12.5 | 0 | 12.5 |
| Z (olefin copolymer) | 1.5 | 1.5 | 1.5 | 0 |
| Transfer index | 1.30 | 1.30 | 1.40 | 1.50 |

It can be observed that the foundations according to the invention (Examples 1 and 2) had a transfer index which is lower than the foundations which contain only the vinyl polymer with a carbosiloxane dendrimer unit (Example 4) or only the olefin copolymer (Example 3).

A synergy is demonstrated here between the two polymers: the combination of the two polymers makes it possible to obtain an improved transfer resistance.

Examples 8 to 12

Five other foundations were prepared in the form of a water-in-oil emulsion having the following formula:

|  |  | Example 8 % by mass | Example 9 % by mass | Example 10 % by mass | Example 11 % by mass | Example 12 % by mass |
|---|---|---|---|---|---|---|
| A1 | Oxyethylenated/oxypropylenated alpha-omega polydimethylsiloxane in cyclopentasiloxane sold under the name Abil EM 97 by the company Goldschmidt | 1.8 | 1.8 | 1.8 | 1.8 | 1.8 |
|  | Isostearyl diglyceryl succinate | 0.5 | 0.5 | 0.5 | 0.5 | 0.5 |
|  | Butyl paraben | 0.25 | 0.25 | 0.25 | 0.25 | 0.25 |
| A2 | Isododecane | 9.45 | 9.45 | 9.45 | 9.45 | 9.45 |
|  | Isohexadecane | 5 | 5 | 5 | 5 | 5 |
|  | Styrene-ethylene/propylene block copolymer sold underthe reference KRATON G1701E by the company Kraton Polymers | 0.9 | 1.1 | 1.1 | 0.9 | 1.6 |
| A3 | Cyclopentasiloxane | 12.7 | 10 | 9 | 10.7 | 12 |
|  | Iron oxides coated with aluminium stearoyl glutamate | 2.83 | 2.83 | 3.27 | 3.35 | 3.96 |
|  | Titanium dioxide coated with aluminium stearoyl glutamate | 9.17 | 9.17 | 10.73 | 10.65 | 8.04 |
| A4 | Polyamide powder (nylon 12) | 7 | 7 | 6 | 7 | 7 |
| B | Demineralized water | 24.25 | 24.25 | 24.25 | 24.25 | 24.25 |
|  | Preservatives | 0.75 | 0.75 | 0.75 | 0.75 | 0.75 |
|  | Magnesium sulphate | 0.7 | 0.7 | 0.7 | 0.7 | 0.7 |
|  | Glycerol | 3 | 3 | 3 | 3 | 3 |
|  | 1-2-octane diol | 0.3 | 0.3 | 0.3 | 0.3 | 0.3 |
| C | Vinyl copolymer containing dendritic silicone side chains in isododecane sold under the name FA 4002 ID by the company Dow Corning. | 12.5 | 15 | 15 | 12.5 | 12.5 |
| D | Hydrophocec pyrogenic silica | 0.3 | 0.3 | 0.3 | 0.3 | 0.3 |
|  | Modified magnesium silicate in isododecane sold under the name Bentone Gel ISD V by the company Elementis | 8 | 8 | 8 | 8 | 8 |
|  | TOTAL | 100 | 100 | 100 | 100 | 100 |

The procedure is the same as the one disclosed in Examples 1 to 7. The foundations thus obtained had a fluid and soft texture and were easy to apply. The make-up obtained unified the complexion while remaining natural and without thickness, it left a comfortable deposit on the face which was soft to the touch and matte. The make-up exhibited a good staying power over time

What is claimed is:

1. A make-up and/or care composition for keratin materials comprising a liquid fatty phase comprising:
   i) vinyl polymer comprising carbosiloxane dendrimer-derived unit, wherein the vinyl polymer comprising unit derived from a carbosiloxane dendrimer is present in the composition in an amount, as active material, ranging from 1% to 10% by weight, relative to the total weight of the composition,
   ii) a styrene-ethylene/propylene copolymer present in the composition in an amount ranging from 0.1% to 10% by weight, relative to the total weight of the composition and iii) at least one volatile oil in an amount ranging from 1 to 80% by weight relative to the total weight of the composition;
   wherein the composition is in the form of an emulsion,
   wherein the vinyl polymer comprising carbosiloxane dendrimer-derived unit is the product of polymerization of:
   (A) from 0.1 to 99.9 parts by weight of at least one monomer chosen from acrylate and methacrylate monomers: and,
   (B) from 100 to 0.1 parts by weight of at least one monomer chosen from acrylate, and methacrylate monomers of a carbosiloxane dendrimer tri[tri(trimethylsiloxy)silylethyl dimethylsiloxy]silylpropyl chosen from the following formulas:

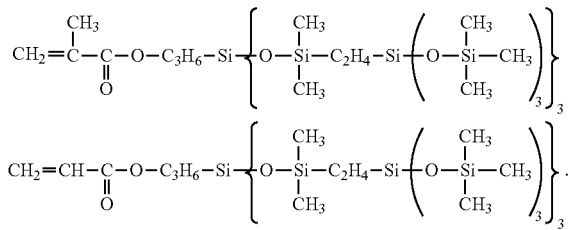

2. The make-up and/or care composition of claim 1, wherein the vinyl polymer comprising unit derived from a carbosiloxane dendrimer is present in the composition in an amount, as active material, ranging from 2% to 7% by weight relative to the total weight of the composition.

3. The make-up and/or care composition of claim 1, wherein styrene-ethylene/propylene copolymer is present in the composition in an amount ranging from 0.5% to 3% by weight relative to the total weight of the composition.

4. The make-up and/or care composition of claim 1, wherein the liquid fatty phase comprises two different volatile oils.

5. The make-up and/or care composition of claim 1, wherein the at least one volatile oil is present in the composition in an amount ranging from 1 to 80% by weight relative to the total weight of the composition.

6. The make-up and/or care composition of claim 5, wherein the at least one volatile oil is present in the composition in an amount ranging from 25 to 55% by weight relative to the total weight of the composition.

7. The make-up and/or care composition of claim 1, further comprising at least one inorganic thickening agent chosen from organophilic clays and pyrogenic silicas.

8. The make-up and/or care composition of claim 1, further comprising at least one pulverulent phase chosen from pigments, fillers, and/or pearlescent agents, and mixtures thereof.

9. The make-up and/or care composition of claim 8, wherein the at least one pulverulent phase comprises at least one polytetrafluoroethylene powder.

10. The make-up and/or care composition of claim 1, further comprising at least one cosmetic ingredient chosen from antioxidants, perfumes, preservatives, neutralizing agents, surfactants, sunscreens, vitamins, moisturizing agents, self-tanning compounds, anti-wrinkle actives, emollients, hydrophilic and lipophilic actives, anti-free radical agents, sequestrants, deodorant agents, film-forming agents, and mixtures thereof.

11. The make-up and/or care composition of claim 1, wherein the composition is provided in the form of a water-in-oil emulsion.

12. A non-therapeutic method for making up and/or caring for keratin materials, comprising applying to the keratin materials at least one composition comprising a liquid fatty phase comprising:
   i) vinyl polymer comprising carbosiloxane dendrimer-derived unit, wherein the vinyl polymer comprising unit derived from a carbosiloxane dendrimer is present in the composition in an amount, as active material, ranging from 1% to 10% by weight, relative to the total weight of the composition,
   ii) a styrene-ethylene/propylene copolymer is present in the composition in an amount ranging from 0.1% to 10% by weight relative to the total weight of the composition and iii) at least one volatile oil in an amount ranging from 1% to 80% by weight relative to the total weight of the composition;
   wherein the composition is in the form of an emulsion,
   wherein the vinyl polymer comprising carbosiloxane dendrimer-derived unit is the product of polymerization of:
   (A) from 0.1 to 99.9 parts by weight of at least one monomer chosen from acrylate and methacrylate monomers; and
   B) from 100 to 0.1 parts by weight of at least one monomer chosen from acrylate and methacrylate monomers of a carbosiloxane dendrimer tri[tri(trimethylsiloxy)silylethyl dimethylsiloxy]silylpropyl chosen from the following formulas:

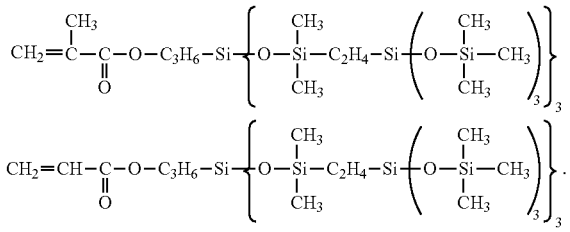

13. A method for producing a make-up on keratin materials which exhibits at least one of improved color fastness, improved matte staying power, and/or improved transfer resistance, the method comprising applying to the keratin materials at least one composition comprising a liquid fatty phase comprising:

i) vinyl polymer comprising carbosiloxane dendrimer-derived unit, wherein the vinyl polymer comprising unit derived from a carbosiloxane dendrimer is present in the composition in an amount, as active material, ranging from 1% to 10% by weight, relative to the total weight of the composition, ii) a styrene-ethylene/propylene copolymer present in the composition in an amount ranging from 0.1% to 10% by weight, relative to the total weight of the composition and iii) at least one volatile oil in an amount ranging from 0.1% to 80% by weight relative to the total weight of the composition;

wherein the composition is in the form of an emulsion, wherein the vinyl polymer comprising carbosiloxane dendrimer-derived unit is the product of polymerization of:

(A) from 0.1 to 99.9 parts by weight of at least one monomer chosen from acrylate and methacrylate monomers: and (B) from 100 to 0.1 parts by weight of at least one monomer chosen from acrylate and methacrvlate monomers of a carbosiloxane dendrimer tri[tri(trimethvIsiloxy)silylethyl dimethylsiloxy]silylpropyl chosen from the following formulas:

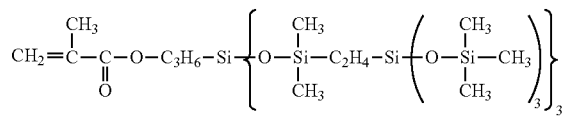

-continued

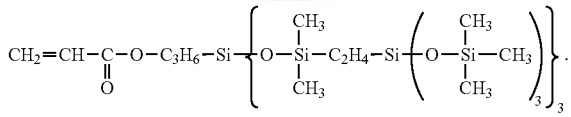

14. The make-up and/or care composition of claim 1, wherein the composition is fluid.

15. The make-up and/or care composition of claim 1, wherein the composition is not in the form of a stick.

16. The make-up and/or care composition of claim 1, wherein the a styrene-ethylene/propylene copolymer is present in the composition in an amount ranging from 0.5% to 3% by weight relative to the total weight of the composition, and wherein the composition is provided in the form of a water-in-oil emulsion.

17. The make-up and/or care composition of claim 1, wherein the a styrene-ethylene/propylene copolymer is present in the composition in an amount ranging from 0.5% to 3% by weight relative to the total weight of the composition, wherein the liquid fatty phase comprises two different volatile oils and at least one volatile oil is present in the composition in an amount ranging from 25 to 55% by weight relative to the total weight of the composition, and wherein the composition is provided in the form of a water-in-oil emulsion.

\* \* \* \* \*

UNITED STATES PATENT AND TRADEMARK OFFICE
CERTIFICATE OF CORRECTION

PATENT NO. : 8,828,372 B2
APPLICATION NO. : 11/806297
DATED : September 9, 2014
INVENTOR(S) : Pascal Arnaud et al.

Page 1 of 1

It is certified that error appears in the above-identified patent and that said Letters Patent is hereby corrected as shown below:

In the Claims

Column 39, line 32, "methacrvlate" should read --methacrylate--;
line 33, "tri[tri(trimethvlsiloxv)" should read --tri[tri(trimethylsiloxy--;
line 34, "dimethylsiloxv]" should read --dimethylsiloxy--;
line 54, "wherein styrene-ethylene/propylene" should read --wherein the styrene-ethylene/propylene--.

Column 40, line 43, "acrvlate" should read --acrylate--;
line 46, "methacrvlate" should read --methacrylate--.

Column 41, line 20, "methacrvlate" should read --methacrylate--;
line 21, "tri[tri(trimethvlsiloxy)" should read --tri[tri(trimethylsiloxy)--.

Column 42, line 13, "where the a styrene-ethylene/propylene copolymer is" should read
--where a styrene-ethylene/propylene copolymer is--;
line 20, "wherein the a styrene-ethylene/propylene copolymer is" should read
--where a styrene-ethylene/propylene copolymer is--.

Signed and Sealed this
Third Day of March, 2015

Michelle K. Lee
*Deputy Director of the United States Patent and Trademark Office*